(12) United States Patent
Gao et al.

(10) Patent No.: US 7,718,362 B2
(45) Date of Patent: May 18, 2010

(54) DNA CHIP BASED GENETIC TYPING

(75) Inventors: Huafang Gao, Beijing (CN); Xuemei Ma, Beijing (CN); Chi Zhang, Beijing (CN); Qian Chen, Beijing (CN); Yiming Zhou, Beijing (CN); Dong Wang, Beijing (CN); Yizhe Zhang, Beijing (CN); Yue Tian, Beijing (CN); Rui Zhang, Beijing (CN); Gengxin Lan, Beijing (CN); Yuxiang Zhou, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 1 day.

(21) Appl. No.: 10/562,803

(22) PCT Filed: Jul. 18, 2003

(86) PCT No.: PCT/CN03/00580

§ 371 (c)(1),
(2), (4) Date: Jun. 30, 2006

(87) PCT Pub. No.: WO2005/001123

PCT Pub. Date: Jan. 6, 2005

(65) Prior Publication Data

US 2007/0134661 A1    Jun. 14, 2007

(30) Foreign Application Priority Data

Jun. 30, 2003   (CN)   ............................ 03 1 48529

(51) Int. Cl.
*C12Q 1/68*    (2006.01)
*C12P 19/34*   (2006.01)
*C12M 1/34*    (2006.01)

(52) U.S. Cl. .................. 435/6; 435/91.2; 435/287.2; 536/23.1; 536/24.3

(58) Field of Classification Search ............... 435/6, 435/91.2, 287.2; 536/23.1, 24.3
See application file for complete search history.

(56) References Cited

U.S. PATENT DOCUMENTS

| | | | |
|---|---|---|---|
| 4,134,792 A | 1/1979 | Boguslaski et al. | |
| 4,230,797 A | 10/1980 | Boguslaski et al. | |
| 4,238,565 A | 12/1980 | Hornby et al. | |
| 4,336,173 A | 6/1982 | Ugelstad et al. | |
| 4,421,660 A | 12/1983 | Solc nee Hajna | |
| 4,490,436 A | 12/1984 | Kawakami et al. | |
| 4,554,088 A | 11/1985 | Whitehead et al. | |
| 4,582,788 A | 4/1986 | Erlich | |
| 4,654,267 A | 3/1987 | Ugelstad et al. | |
| 4,683,195 A | 7/1987 | Mullis et al. | |
| 4,683,202 A | 7/1987 | Mullis | |
| 4,774,265 A | 9/1988 | Ugelstad et al. | |
| 4,800,159 A | 1/1989 | Mullis et al. | |
| 4,965,007 A | 10/1990 | Yudelson | |
| 4,965,188 A | 10/1990 | Mullis et al. | |
| 5,091,206 A | 2/1992 | Wang et al. | |
| 5,119,801 A | 6/1992 | Eizenhoefer et al. | |
| 5,130,238 A | 7/1992 | Malek et al. | |
| 5,143,854 A | 9/1992 | Pirrung et al. | |
| 5,232,782 A | 8/1993 | Charmot | |
| 5,270,184 A | 12/1993 | Walker et al. | |
| 5,283,079 A | 2/1994 | Wang et al. | |
| 5,288,514 A | 2/1994 | Ellman | |
| 5,312,233 A | 5/1994 | Tanny et al. | |
| 5,312,728 A | 5/1994 | Lizardi et al. | |
| 5,318,797 A | 6/1994 | Matijevic et al. | |
| 5,348,855 A | 9/1994 | Dattagupta et al. | |
| 5,384,261 A | 1/1995 | Winkler et al. | |
| 5,395,688 A | 3/1995 | Wang et al. | |
| 5,541,061 A | 7/1996 | Fodor et al. | |
| 5,545,531 A | 8/1996 | Rava et al. | |
| 5,556,752 A | 9/1996 | Lockhart et al. | |
| 5,561,071 A | 10/1996 | Hollenberg et al. | |
| 5,567,809 A * | 10/1996 | Apple et al. ............... 536/24.3 |

(Continued)

FOREIGN PATENT DOCUMENTS

CN    1347958    5/2002

(Continued)

OTHER PUBLICATIONS

Trau et al, Genotyping on a complementary metal oxide semiconductor silicon polymerase chain reaction chip with integrated DNA microarray, 2002, Anal. Chem., 74, 3168-3173.*

(Continued)

*Primary Examiner*—Stephen Kapushoc
*Assistant Examiner*—Narayan K Bhat
(74) *Attorney, Agent, or Firm*—Morrison & Foerster LLP

(57) ABSTRACT

This invention relates generally to the field of nucleic acid analysis. In particular, the invention provides a method for typing a target gene, using, inter alia, a chip comprising a support suitable for use in nucleic acid hybridization having immobilized thereon an oligonucleotide probe complementary to said target nucleotide sequence and at least one of the following oligonucleotide control probes: a positive control probe, a negative control probe, a hybridization control probe and an immobilization control probe. Oligonucleotide probes or probes arrays for typing a HLA target gene are also provided.

23 Claims, 4 Drawing Sheets

U.S. PATENT DOCUMENTS

| | | | |
|---|---|---|---|
| 5,648,211 | A | 7/1997 | Fraiser et al. |
| 5,677,195 | A | 10/1997 | Winkler et al. |
| 5,702,885 | A | 12/1997 | Baxter-Lowe et al. |
| 5,834,121 | A | 11/1998 | Sucholeiki et al. |
| 5,843,640 | A * | 12/1998 | Patterson et al. ............... 435/5 |
| 6,004,745 | A | 12/1999 | Arnold, Jr. et al. |
| 6,024,138 | A | 2/2000 | Fritz et al. |
| 6,150,097 | A | 11/2000 | Tyagi et al. |
| 6,156,508 | A | 12/2000 | Spears et al. |
| 6,300,076 | B1 | 10/2001 | Koster |
| 6,465,183 | B2 | 10/2002 | Wolber |
| 2002/0051973 | A1 * | 5/2002 | Delenstarr et al. ............. 435/6 |
| 2002/0086289 | A1 * | 7/2002 | Straus ........................ 435/6 |
| 2002/0187505 | A1 * | 12/2002 | Stockton ....................... 435/6 |
| 2003/0054378 | A1 | 3/2003 | Karube et al. |
| 2003/0119178 | A1 | 6/2003 | Sato et al. |

FOREIGN PATENT DOCUMENTS

| | | |
|---|---|---|
| CN | 1392268 | 1/2003 |
| CN | 1400315 | 3/2003 |
| CN | 1405322 | 3/2003 |
| EP | 0 684 315 | 11/1995 |
| EP | 1 096 024 | 5/2001 |
| GB | 1548741 | 7/1979 |
| WO | WO-98/51693 | 11/1998 |
| WO | WO-00/79006 | 12/2000 |
| WO | WO 00/79006 | * 12/2000 |
| WO | WO-02/18646 | 3/2002 |
| WO | WO-02/075309 | 9/2002 |

OTHER PUBLICATIONS

Samartzidou et al, Lucidea microarray scorecard: An integrated tool for validation of microarray gene expression experiments, 2001, Life science news, 8, 1-3.*
Sequence Alignment brochure 1.*
Sequence alignment brochure 2.*
Chen et al., Journal of Huazhong University of Science and Technology (2004) 24(1):25-27.
Deggerdal et al., Biotechniques (1997) 22(3):554-557.
Eliaou et al., Human Immunology (1992) 35(4):215-222.
Gao et al., Human Immunology (1994) 41(4):267-279.
Rudi et al., Biotechniques (1997) 22(3):506-511.
Supplementary European Search Report for EP 03817285.4, mailed on Mar. 27, 2007, 7 pages.
Bleaney and Bleaney, Chapter 6 in "Electricity and Magnetism" Oxford (1975) pp. 169-174.
Bleaney and Bleaney, Chapter 16 in "Electricity and Magnetism" Oxford (1975) pp. 519-524.
Broude et al., Nucleic Acids Res. (2001) 29(19):E92.
Cao et al., Rev. Immunogenet. (1999) 1:177-208.
Dattagupta et al., Analytical Biochemistry (1989) 177:85-89.
Forster et al., Nucleic Acid Res. (1985) 13:745.
Gorus and Schram, Clin. Chem. (1979) 25:512-519.
Gravitt et al., J. Clin. Micro. (1998) 36:3020-3027.
Guo et al., Rev. Immunogenet. (1999) 1:220-230.
Hertzberg et al., J. Amer. Chem. Soc. (1982) 104:313.
International Search Report for PCT/CN03/00580, mailed on Jul. 29, 2004, 3 pages.
Kahiwase, Rinsho Byori Suppl. (1999) 110:99-106.
Kwoh et al., PNAS USA (1989) 86:1173-1177.
Matijevic, Acc. Chem. Res. (1981) 14:22-29.
Matteucci et al., J. Am. Chem. Soc. (1981) 3:3185-3191.
Milligan et al., J. Med. Chem. (1993) 36:1923.
Mitchell et al., J. Am. Chem. Soc. (1982) 104:4265.
Mytilineos et al., Hum. Immunol. (1998) 59:512-517.
Saiki et al., PNAS USA (1989) 86:6230-6234.
Shaw et al., Nucleic Acids Res. (1991) 19:747.
Soini and Hemmila, Clin. Chem. (1979) 25:353-361.
Tian Zhenjun et al., Chin. J. Sports Med. (2002) 21(2).
Tyagi et al., Nature Biotechnology (1996) 14:303-308.
Vandenberghe et al., J. of Magnetism and Magnetic Materials (1980) 15-18:1117-1118.
White et al., Meth. Enzymol. (1977) 46:644.
Whitehead et al., Clin. Chem. (1979) 25:1531-1546.
Wisdom, Clin. Chem. (1976) 22:1243.
Wood et al., PNAS USA (1985) 82:1585-1588.

* cited by examiner

SEQUENCE LISTING

<160> NUMBER OF SEQ ID NOS: 214

<210> SEQ ID NO 1
<211> LENGTH: 18
<212> TYPE: DNA
<213> ORGANISM: Artificial Sequence
<220> FEATURE:
<223> OTHER INFORMATION: Probe

<400> SEQUENCE: 1
cctgcgctct tggaccgc                                                 18

<210> SEQ ID NO 2
<211> LENGTH: 19
<212> TYPE: DNA
<213> ORGANISM: Artificial Sequence
<220> FEATURE:
<223> OTHER INFORMATION: Probe

<400> SEQUENCE: 2
cctgcgctct tggaccgcg                                                19

<210> SEQ ID NO 3
<211> LENGTH: 20
<212> TYPE: DNA
<213> ORGANISM: Artificial Sequence
<220> FEATURE:
<223> OTHER INFORMATION: Probe

<400> SEQUENCE: 3
cctcctgcgc tcttggaccg                                               20

```
<210> SEQ ID NO 4
<211> LENGTH: 16
<212> TYPE: DNA
<213> ORGANISM: Artificial Sequence
<220> FEATURE:
<223> OTHER INFORMATION: Probe

<400> SEQUENCE: 4
cctgcgctct tggacc                                                    16

<210> SEQ ID NO 5
<211> LENGTH: 16
<212> TYPE: DNA
<213> ORGANISM: Artificial Sequence
<220> FEATURE:
<223> OTHER INFORMATION: Probe

<400> SEQUENCE: 5
cgtgtcccgg cccggc                                                    16

<210> SEQ ID NO 6
<211> LENGTH: 16
<212> TYPE: DNA
<213> ORGANISM: Artificial Sequence
<220> FEATURE:
<223> OTHER INFORMATION: Probe

<400> SEQUENCE: 6
atggagccgc gggcgc                                                    16

<210> SEQ ID NO 7
<211> LENGTH: 20
<212> TYPE: DNA
<213> ORGANISM: Artificial Sequence
<220> FEATURE:
<223> OTHER INFORMATION: Probe

<400> SEQUENCE: 7
cctgcgctct tggaccgcgg                                                20

<210> SEQ ID NO 8
<211> LENGTH: 18
<212> TYPE: DNA
<213> ORGANISM: Artificial Sequence
<220> FEATURE:
<223> OTHER INFORMATION: Probe

<400> SEQUENCE: 8
gcggtccaag agcgcagg                                                  18

<210> SEQ ID NO 9
<211> LENGTH: 18
<212> TYPE: DNA
<213> ORGANISM: Artificial Sequence
<220> FEATURE:
<223> OTHER INFORMATION: Probe

<400> SEQUENCE: 9
cctgcgcttt tggaccgc                                                  18

<210> SEQ ID NO 10
<211> LENGTH: 18
<212> TYPE: DNA
<213> ORGANISM: Artificial Sequence
<220> FEATURE:
```

```
<223> OTHER INFORMATION: Probe

<400> SEQUENCE: 10
cctgcgctgt tggaccgc                                                    18

<210> SEQ ID NO 11
<211> LENGTH: 22
<212> TYPE: DNA
<213> ORGANISM: Artificial Sequence
<220> FEATURE:
<223> OTHER INFORMATION: Probe

<400> SEQUENCE: 11
gcaggagagg cctgagtatt gg                                               22

<210> SEQ ID NO 12
<211> LENGTH: 24
<212> TYPE: DNA
<213> ORGANISM: Artificial Sequence
<220> FEATURE:
<223> OTHER INFORMATION: Probe

<400> SEQUENCE: 12
caccatcaga taatgtatgg ctgc                                             24

<210> SEQ ID NO 13
<211> LENGTH: 25
<212> TYPE: DNA
<213> ORGANISM: Artificial Sequence
<220> FEATURE:
<223> OTHER INFORMATION: Probe

<400> SEQUENCE: 13
caccatccag ataatgtatg gctgc                                            25

<210> SEQ ID NO 14
<211> LENGTH: 20
<212> TYPE: DNA
<213> ORGANISM: Artificial Sequence
<220> FEATURE:
<223> OTHER INFORMATION: Probe

<400> SEQUENCE: 14
ttctacacct ccgtgtcccg                                                  20

<210> SEQ ID NO 15
<211> LENGTH: 19
<212> TYPE: DNA
<213> ORGANISM: Artificial Sequence
<220> FEATURE:
<223> OTHER INFORMATION: Probe

<400> SEQUENCE: 15
cgcttcatcg cagtgggct                                                   19

<210> SEQ ID NO 16
<211> LENGTH: 19
<212> TYPE: DNA
<213> ORGANISM: Artificial Sequence
<220> FEATURE:
<223> OTHER INFORMATION: Probe

<400> SEQUENCE: 16
cgagccagaa gatggagcc                                                   19
```

```
<210> SEQ ID NO 17
<211> LENGTH: 18
<212> TYPE: DNA
<213> ORGANISM: Artificial Sequence
<220> FEATURE:
<223> OTHER INFORMATION: Probe

<400> SEQUENCE: 17
ccgcgggcac cgtggata                                                   18

<210> SEQ ID NO 18
<211> LENGTH: 20
<212> TYPE: DNA
<213> ORGANISM: Artificial Sequence
<220> FEATURE:
<223> OTHER INFORMATION: Probe

<400> SEQUENCE: 18
gcaggagggt ccggagtatt                                                 20

<210> SEQ ID NO 19
<211> LENGTH: 18
<212> TYPE: DNA
<213> ORGANISM: Artificial Sequence
<220> FEATURE:
<223> OTHER INFORMATION: Probe

<400> SEQUENCE: 19
gacgtggggc cggacggg                                                   18

<210> SEQ ID NO 20
<211> LENGTH: 18
<212> TYPE: DNA
<213> ORGANISM: Artificial Sequence
<220> FEATURE:
<223> OTHER INFORMATION: Probe

<400> SEQUENCE: 20
gacgggcgcc tcctccgc                                                   18

<210> SEQ ID NO 21
<211> LENGTH: 20
<212> TYPE: DNA
<213> ORGANISM: Artificial Sequence
<220> FEATURE:
<223> OTHER INFORMATION: Probe

<400> SEQUENCE: 21
cgggtaccac cagtacgcct                                                 20

<210> SEQ ID NO 22
<211> LENGTH: 19
<212> TYPE: DNA
<213> ORGANISM: Artificial Sequence
<220> FEATURE:
<223> OTHER INFORMATION: Probe

<400> SEQUENCE: 22
ggtaccggca ggacgccta                                                  19

<210> SEQ ID NO 23
<211> LENGTH: 19
<212> TYPE: DNA
<213> ORGANISM: Artificial Sequence
<220> FEATURE:
<223> OTHER INFORMATION: Probe
```

-continued

```
<400> SEQUENCE: 23
cgccctgaac gaggacctg                                              19

<210> SEQ ID NO 24
<211> LENGTH: 20
<212> TYPE: DNA
<213> ORGANISM: Artificial Sequence
<220> FEATURE:
<223> OTHER INFORMATION: Probe

<400> SEQUENCE: 24
cggacatggc agctcagatc                                             20

<210> SEQ ID NO 25
<211> LENGTH: 19
<212> TYPE: DNA
<213> ORGANISM: Artificial Sequence
<220> FEATURE:
<223> OTHER INFORMATION: Probe

<400> SEQUENCE: 25
ccaccaagca caagtggga                                              19

<210> SEQ ID NO 26
<211> LENGTH: 19
<212> TYPE: DNA
<213> ORGANISM: Artificial Sequence
<220> FEATURE:
<223> OTHER INFORMATION: Probe

<400> SEQUENCE: 26
aagtgggaga cggcccatg                                              19

<210> SEQ ID NO 27
<211> LENGTH: 18
<212> TYPE: DNA
<213> ORGANISM: Artificial Sequence
<220> FEATURE:
<223> OTHER INFORMATION: Probe

<400> SEQUENCE: 27
aggcggcccg tgtggcgg                                               18

<210> SEQ ID NO 28
<211> LENGTH: 18
<212> TYPE: DNA
<213> ORGANISM: Artificial Sequence
<220> FEATURE:
<223> OTHER INFORMATION: Probe

<400> SEQUENCE: 28
aggcggtcca tgcggcgg                                               18

<210> SEQ ID NO 29
<211> LENGTH: 18
<212> TYPE: DNA
<213> ORGANISM: Artificial Sequence
<220> FEATURE:
<223> OTHER INFORMATION: Probe

<400> SEQUENCE: 29
cggcccatga ggcggagc                                               18

<210> SEQ ID NO 30
<211> LENGTH: 19
```

<212> TYPE: DNA
<213> ORGANISM: Artificial Sequence
<220> FEATURE:
<223> OTHER INFORMATION: Probe

<400> SEQUENCE: 30
tacctggatg gcacgtgcg                                                    19

<210> SEQ ID NO 31
<211> LENGTH: 19
<212> TYPE: DNA
<213> ORGANISM: Artificial Sequence
<220> FEATURE:
<223> OTHER INFORMATION: Probe

<400> SEQUENCE: 31
ctggagggcg agtgcgtgg                                                    19

<210> SEQ ID NO 32
<211> LENGTH: 18
<212> TYPE: DNA
<213> ORGANISM: Artificial Sequence
<220> FEATURE:
<223> OTHER INFORMATION: Probe

<400> SEQUENCE: 32
tgcgtggacg ggctccgc                                                     18

<210> SEQ ID NO 33
<211> LENGTH: 24
<212> TYPE: DNA
<213> ORGANISM: Artificial Sequence
<220> FEATURE:
<223> OTHER INFORMATION: Probe

<400> SEQUENCE: 33
gtatttctac acctccgtgt cccg                                              24

<210> SEQ ID NO 34
<211> LENGTH: 19
<212> TYPE: DNA
<213> ORGANISM: Artificial Sequence
<220> FEATURE:
<223> OTHER INFORMATION: Probe

<400> SEQUENCE: 34
cgagcggttt gacagcgac                                                    19

<210> SEQ ID NO 35
<211> LENGTH: 19
<212> TYPE: DNA
<213> ORGANISM: Artificial Sequence
<220> FEATURE:
<223> OTHER INFORMATION: Probe

<400> SEQUENCE: 35
cgtgcggttc gacagcgac                                                    19

<210> SEQ ID NO 36
<211> LENGTH: 16
<212> TYPE: DNA
<213> ORGANISM: Artificial Sequence
<220> FEATURE:
<223> OTHER INFORMATION: Probe

<400> SEQUENCE: 36

-continued cgtggggccg gacggg                                                    16

<210> SEQ ID NO 37
<211> LENGTH: 17
<212> TYPE: DNA
<213> ORGANISM: Artificial Sequence
<220> FEATURE:
<223> OTHER INFORMATION: Probe

<400> SEQUENCE: 37
aggcggtcca tgcggcg                                                   17

<210> SEQ ID NO 38
<211> LENGTH: 18
<212> TYPE: DNA
<213> ORGANISM: Artificial Sequence
<220> FEATURE:
<223> OTHER INFORMATION: Probe

<400> SEQUENCE: 38
cccggccgcg gggagccc                                                  18

<210> SEQ ID NO 39
<211> LENGTH: 18
<212> TYPE: DNA
<213> ORGANISM: Artificial Sequence
<220> FEATURE:
<223> OTHER INFORMATION: Probe

<400> SEQUENCE: 39
ccgcgggcgc cgtggata                                                  18

<210> SEQ ID NO 40
<211> LENGTH: 19
<212> TYPE: DNA
<213> ORGANISM: Artificial Sequence
<220> FEATURE:
<223> OTHER INFORMATION: Probe

<400> SEQUENCE: 40
tgggacgagg agacaggga                                                 19

<210> SEQ ID NO 41
<211> LENGTH: 19
<212> TYPE: DNA
<213> ORGANISM: Artificial Sequence
<220> FEATURE:
<223> OTHER INFORMATION: Probe

<400> SEQUENCE: 41
tgggaccagg agacacgga                                                 19

<210> SEQ ID NO 42
<211> LENGTH: 19
<212> TYPE: DNA
<213> ORGANISM: Artificial Sequence
<220> FEATURE:
<223> OTHER INFORMATION: Probe

<400> SEQUENCE: 42
tggggaccct gcgcggcta                                                 19

<210> SEQ ID NO 43
<211> LENGTH: 18
<212> TYPE: DNA
<213> ORGANISM: Artificial Sequence

```
<220> FEATURE:
<223> OTHER INFORMATION: Probe

<400> SEQUENCE: 43
gacgtggggt cggacggg                                                 18

<210> SEQ ID NO 44
<211> LENGTH: 18
<212> TYPE: DNA
<213> ORGANISM: Artificial Sequence
<220> FEATURE:
<223> OTHER INFORMATION: Probe

<400> SEQUENCE: 44
gacgggcgct tcctccgc                                                 18

<210> SEQ ID NO 45
<211> LENGTH: 19
<212> TYPE: DNA
<213> ORGANISM: Artificial Sequence
<220> FEATURE:
<223> OTHER INFORMATION: Probe

<400> SEQUENCE: 45
gcgggtacca gcaggacgc                                                19

<210> SEQ ID NO 46
<211> LENGTH: 19
<212> TYPE: DNA
<213> ORGANISM: Artificial Sequence
<220> FEATURE:
<223> OTHER INFORMATION: Probe

<400> SEQUENCE: 46
cgccctgaaa gaggacctg                                                19

<210> SEQ ID NO 47
<211> LENGTH: 20
<212> TYPE: DNA
<213> ORGANISM: Artificial Sequence
<220> FEATURE:
<223> OTHER INFORMATION: Probe

<400> SEQUENCE: 47
agctcagatc accaagcgca                                               20

<210> SEQ ID NO 48
<211> LENGTH: 21
<212> TYPE: DNA
<213> ORGANISM: Artificial Sequence
<220> FEATURE:
<223> OTHER INFORMATION: Probe

<400> SEQUENCE: 48
tcagatcacc aagcgcaaga g                                             21

<210> SEQ ID NO 49
<211> LENGTH: 20
<212> TYPE: DNA
<213> ORGANISM: Artificial Sequence
<220> FEATURE:
<223> OTHER INFORMATION: Probe

<400> SEQUENCE: 49
agctcagatc accgagcgca                                               20
```

<210> SEQ ID NO 50
<211> LENGTH: 20
<212> TYPE: DNA
<213> ORGANISM: Artificial Sequence
<220> FEATURE:
<223> OTHER INFORMATION: Probe

<400> SEQUENCE: 50
ggctcagatc acccagcgca                                               20

<210> SEQ ID NO 51
<211> LENGTH: 21
<212> TYPE: DNA
<213> ORGANISM: Artificial Sequence
<220> FEATURE:
<223> OTHER INFORMATION: Probe

<400> SEQUENCE: 51
tcagatcacc cagcgcaagt g                                             21

<210> SEQ ID NO 52
<211> LENGTH: 17
<212> TYPE: DNA
<213> ORGANISM: Artificial Sequence
<220> FEATURE:
<223> OTHER INFORMATION: Probe

<400> SEQUENCE: 52
agacggccca tgaggcg                                                  17

<210> SEQ ID NO 53
<211> LENGTH: 18
<212> TYPE: DNA
<213> ORGANISM: Artificial Sequence
<220> FEATURE:
<223> OTHER INFORMATION: Probe

<400> SEQUENCE: 53
agacggccca tgaggcgg                                                 18

<210> SEQ ID NO 54
<211> LENGTH: 19
<212> TYPE: DNA
<213> ORGANISM: Artificial Sequence
<220> FEATURE:
<223> OTHER INFORMATION: Probe

<400> SEQUENCE: 54
gcggagcagc ggagagtct                                                19

<210> SEQ ID NO 55
<211> LENGTH: 18
<212> TYPE: DNA
<213> ORGANISM: Artificial Sequence
<220> FEATURE:
<223> OTHER INFORMATION: Probe

<400> SEQUENCE: 55
agacggccca tgaggcgg                                                 18

<210> SEQ ID NO 56
<211> LENGTH: 19
<212> TYPE: DNA
<213> ORGANISM: Artificial Sequence
<220> FEATURE:
<223> OTHER INFORMATION: Probe

<400> SEQUENCE: 56
gcggagcagt tgagagcct          19

<210> SEQ ID NO 57
<211> LENGTH: 19
<212> TYPE: DNA
<213> ORGANISM: Artificial Sequence
<220> FEATURE:
<223> OTHER INFORMATION: Probe

<400> SEQUENCE: 57
ggcggagcag ttgagagcc          19

<210> SEQ ID NO 58
<211> LENGTH: 19
<212> TYPE: DNA
<213> ORGANISM: Artificial Sequence
<220> FEATURE:
<223> OTHER INFORMATION: Probe

<400> SEQUENCE: 58
gcggagcagt ggagagcct          19

<210> SEQ ID NO 59
<211> LENGTH: 19
<212> TYPE: DNA
<213> ORGANISM: Artificial Sequence
<220> FEATURE:
<223> OTHER INFORMATION: Probe

<400> SEQUENCE: 59
tacctggagg gcacgtgcg          19

<210> SEQ ID NO 60
<211> LENGTH: 18
<212> TYPE: DNA
<213> ORGANISM: Artificial Sequence
<220> FEATURE:
<223> OTHER INFORMATION: Probe

<400> SEQUENCE: 60
tgcgtggagt ggctccgc          18

<210> SEQ ID NO 61
<211> LENGTH: 19
<212> TYPE: DNA
<213> ORGANISM: Artificial Sequence
<220> FEATURE:
<223> OTHER INFORMATION: Probe

<400> SEQUENCE: 61
tcaccgagtg gacctgggg          19

<210> SEQ ID NO 62
<211> LENGTH: 19
<212> TYPE: DNA
<213> ORGANISM: Artificial Sequence
<220> FEATURE:
<223> OTHER INFORMATION: Probe

<400> SEQUENCE: 62
ccgagtggac ctggggacc          19

<210> SEQ ID NO 63

```
<211> LENGTH: 19
<212> TYPE: DNA
<213> ORGANISM: Artificial Sequence
<220> FEATURE:
<223> OTHER INFORMATION: Probe

<400> SEQUENCE: 63
tgaccgagag aacctgcgg                                                   19

<210> SEQ ID NO 64
<211> LENGTH: 20
<212> TYPE: DNA
<213> ORGANISM: Artificial Sequence
<220> FEATURE:
<223> OTHER INFORMATION: Probe

<400> SEQUENCE: 64
ccgagagaac ctgcggatcg                                                  20

<210> SEQ ID NO 65
<211> LENGTH: 20
<212> TYPE: DNA
<213> ORGANISM: Artificial Sequence
<220> FEATURE:
<223> OTHER INFORMATION: Probe

<400> SEQUENCE: 65
gaaggcccac tcacagactg                                                  20

<210> SEQ ID NO 66
<211> LENGTH: 23
<212> TYPE: DNA
<213> ORGANISM: Artificial Sequence
<220> FEATURE:
<223> OTHER INFORMATION: Probe

<400> SEQUENCE: 66
tatttcttca catccgtgtc ccg                                              23

<210> SEQ ID NO 67
<211> LENGTH: 21
<212> TYPE: DNA
<213> ORGANISM: Artificial Sequence
<220> FEATURE:
<223> OTHER INFORMATION: Probe

<400> SEQUENCE: 67
tctacacttc cgtttcccgg c                                                21

<210> SEQ ID NO 68
<211> LENGTH: 20
<212> TYPE: DNA
<213> ORGANISM: Artificial Sequence
<220> FEATURE:
<223> OTHER INFORMATION: Probe

<400> SEQUENCE: 68
ctacacctcc atgtcccggc                                                  20

<210> SEQ ID NO 69
<211> LENGTH: 21
<212> TYPE: DNA
<213> ORGANISM: Artificial Sequence
<220> FEATURE:
<223> OTHER INFORMATION: Probe

<400> SEQUENCE: 69
```
ccggaacaca cggaaagtga a                                    21

<210> SEQ ID NO 70
<211> LENGTH: 19
<212> TYPE: DNA
<213> ORGANISM: Artificial Sequence
<220> FEATURE:
<223> OTHER INFORMATION: Probe

<400> SEQUENCE: 70
attgggacgg ggagacacg                                       19

<210> SEQ ID NO 71
<211> LENGTH: 21
<212> TYPE: DNA
<213> ORGANISM: Artificial Sequence
<220> FEATURE:
<223> OTHER INFORMATION: Probe

<400> SEQUENCE: 71
gacacggaat atgaaggccc a                                    21

<210> SEQ ID NO 72
<211> LENGTH: 20
<212> TYPE: DNA
<213> ORGANISM: Artificial Sequence
<220> FEATURE:
<223> OTHER INFORMATION: Probe

<400> SEQUENCE: 72
gacacggaat gtgaaggccc                                      20

<210> SEQ ID NO 73
<211> LENGTH: 22
<212> TYPE: DNA
<213> ORGANISM: Artificial Sequence
<220> FEATURE:
<223> OTHER INFORMATION: Probe

<400> SEQUENCE: 73
tcacagactc accgagtgga cc                                   22

<210> SEQ ID NO 74
<211> LENGTH: 22
<212> TYPE: DNA
<213> ORGANISM: Artificial Sequence
<220> FEATURE:
<223> OTHER INFORMATION: Probe

<400> SEQUENCE: 74
tcacagattg accgagtgga cc                                   22

<210> SEQ ID NO 75
<211> LENGTH: 22
<212> TYPE: DNA
<213> ORGANISM: Artificial Sequence
<220> FEATURE:
<223> OTHER INFORMATION: Probe

<400> SEQUENCE: 75
tcacagactg accgagtgga cc                                   22

<210> SEQ ID NO 76
<211> LENGTH: 18
<212> TYPE: DNA

-continued

```
<213> ORGANISM: Artificial Sequence
<220> FEATURE:
<223> OTHER INFORMATION: Probe

<400> SEQUENCE: 76
cgagcgaacc tgggacc                                                       18

<210> SEQ ID NO 77
<211> LENGTH: 19
<212> TYPE: DNA
<213> ORGANISM: Artificial Sequence
<220> FEATURE:
<223> OTHER INFORMATION: Probe

<400> SEQUENCE: 77
ccgagagagc ctgcggatc                                                     19

<210> SEQ ID NO 78
<211> LENGTH: 20
<212> TYPE: DNA
<213> ORGANISM: Artificial Sequence
<220> FEATURE:
<223> OTHER INFORMATION: Probe

<400> SEQUENCE: 78
accgagagaa cctggggacc                                                    20

<210> SEQ ID NO 79
<211> LENGTH: 19
<212> TYPE: DNA
<213> ORGANISM: Artificial Sequence
<220> FEATURE:
<223> OTHER INFORMATION: Probe

<400> SEQUENCE: 79
gtggacctgg cgaccctgc                                                     19

<210> SEQ ID NO 80
<211> LENGTH: 22
<212> TYPE: DNA
<213> ORGANISM: Artificial Sequence
<220> FEATURE:
<223> OTHER INFORMATION: Probe

<400> SEQUENCE: 80
caccgtccag aggatgtatg gc                                                 22

<210> SEQ ID NO 81
<211> LENGTH: 21
<212> TYPE: DNA
<213> ORGANISM: Artificial Sequence
<220> FEATURE:
<223> OTHER INFORMATION: Probe

<400> SEQUENCE: 81
accagcagga cgcttacgac g                                                  21

<210> SEQ ID NO 82
<211> LENGTH: 20
<212> TYPE: DNA
<213> ORGANISM: Artificial Sequence
<220> FEATURE:
<223> OTHER INFORMATION: Probe

<400> SEQUENCE: 82
tcgccttgaa cgaggacctg                                                    20
```

```
<210> SEQ ID NO 83
<211> LENGTH: 18
<212> TYPE: DNA
<213> ORGANISM: Artificial Sequence
<220> FEATURE:
<223> OTHER INFORMATION: Probe

<400> SEQUENCE: 83
cctgcgctct tggaccgc                                                 18

<210> SEQ ID NO 84
<211> LENGTH: 22
<212> TYPE: DNA
<213> ORGANISM: Artificial Sequence
<220> FEATURE:
<223> OTHER INFORMATION: Probe

<400> SEQUENCE: 84
tcagaccacc aagcacaagt gg                                            22

<210> SEQ ID NO 85
<211> LENGTH: 17
<212> TYPE: DNA
<213> ORGANISM: Artificial Sequence
<220> FEATURE:
<223> OTHER INFORMATION: Probe

<400> SEQUENCE: 85
gaggcggccc atgtggc                                                  17

<210> SEQ ID NO 86
<211> LENGTH: 17
<212> TYPE: DNA
<213> ORGANISM: Artificial Sequence
<220> FEATURE:
<223> OTHER INFORMATION: Probe

<400> SEQUENCE: 86
ggcccatgcg gcggagc                                                  17

<210> SEQ ID NO 87
<211> LENGTH: 17
<212> TYPE: DNA
<213> ORGANISM: Artificial Sequence
<220> FEATURE:
<223> OTHER INFORMATION: Probe

<400> SEQUENCE: 87
gcggcccgtc gggcgga                                                  17

<210> SEQ ID NO 88
<211> LENGTH: 18
<212> TYPE: DNA
<213> ORGANISM: Artificial Sequence
<220> FEATURE:
<223> OTHER INFORMATION: Probe

<400> SEQUENCE: 88
gcacgtgcgt ggagtggc                                                 18

<210> SEQ ID NO 89
<211> LENGTH: 18
<212> TYPE: DNA
<213> ORGANISM: Artificial Sequence
<220> FEATURE:
```

<223> OTHER INFORMATION: Probe

<400> SEQUENCE: 89
gccggtgcgt ggacgggc                                          18

<210> SEQ ID NO 90
<211> LENGTH: 19
<212> TYPE: DNA
<213> ORGANISM: Artificial Sequence
<220> FEATURE:
<223> OTHER INFORMATION: Probe

<400> SEQUENCE: 90
ggcgagtgcg tggagtggc                                         19

<210> SEQ ID NO 91
<211> LENGTH: 18
<212> TYPE: DNA
<213> ORGANISM: Artificial Sequence
<220> FEATURE:
<223> OTHER INFORMATION: Probe

<400> SEQUENCE: 91
gcacgtgcgt ggacgggc                                          18

<210> SEQ ID NO 92
<211> LENGTH: 18
<212> TYPE: DNA
<213> ORGANISM: Artificial Sequence
<220> FEATURE:
<223> OTHER INFORMATION: Probe

<400> SEQUENCE: 92
gccggtgcgt ggagtggc                                          18

<210> SEQ ID NO 93
<211> LENGTH: 19
<212> TYPE: DNA
<213> ORGANISM: Artificial Sequence
<220> FEATURE:
<223> OTHER INFORMATION: Probe

<400> SEQUENCE: 93
ggcgagtgcg tggacgggc                                         19

<210> SEQ ID NO 94
<211> LENGTH: 21
<212> TYPE: DNA
<213> ORGANISM: Artificial Sequence
<220> FEATURE:
<223> OTHER INFORMATION: Probe

<400> SEQUENCE: 94
agacacggaa agtgaaggcc c                                      21

<210> SEQ ID NO 95
<211> LENGTH: 22
<212> TYPE: DNA
<213> ORGANISM: Artificial Sequence
<220> FEATURE:
<223> OTHER INFORMATION: Probe

<400> SEQUENCE: 95
tggccctgac cgagacctgg gc                                     22

```
<210> SEQ ID NO 96
<211> LENGTH: 20
<212> TYPE: DNA
<213> ORGANISM: Artificial Sequence
<220> FEATURE:
<223> OTHER INFORMATION: Probe

<400> SEQUENCE: 96
ctacaaccag agcgaggccg                                               20

<210> SEQ ID NO 97
<211> LENGTH: 19
<212> TYPE: DNA
<213> ORGANISM: Artificial Sequence
<220> FEATURE:
<223> OTHER INFORMATION: Probe

<400> SEQUENCE: 97
gccctgaccc agacctggg                                                19

<210> SEQ ID NO 98
<211> LENGTH: 18
<212> TYPE: DNA
<213> ORGANISM: Artificial Sequence
<220> FEATURE:
<223> OTHER INFORMATION: Probe

<400> SEQUENCE: 98
cccgaaccct cctcctgc                                                 18

<210> SEQ ID NO 99
<211> LENGTH: 18
<212> TYPE: DNA
<213> ORGANISM: Artificial Sequence
<220> FEATURE:
<223> OTHER INFORMATION: Probe

<400> SEQUENCE: 99
cccgaaccgt cctcctgc                                                 18

<210> SEQ ID NO 100
<211> LENGTH: 17
<212> TYPE: DNA
<213> ORGANISM: Artificial Sequence
<220> FEATURE:
<223> OTHER INFORMATION: Probe

<400> SEQUENCE: 100
tgctctcggc ggccctg                                                  17

<210> SEQ ID NO 101
<211> LENGTH: 18
<212> TYPE: DNA
<213> ORGANISM: Artificial Sequence
<220> FEATURE:
<223> OTHER INFORMATION: Probe

<400> SEQUENCE: 101
tgctctcggg agccctgg                                                 18

<210> SEQ ID NO 102
<211> LENGTH: 16
<212> TYPE: DNA
<213> ORGANISM: Artificial Sequence
<220> FEATURE:
<223> OTHER INFORMATION: Probe
```

```
<400> SEQUENCE: 102 gggggggcagt ggccct                                                      16

<210> SEQ ID NO 103
<211> LENGTH: 21
<212> TYPE: DNA
<213> ORGANISM: Artificial Sequence
<220> FEATURE:
<223> OTHER INFORMATION: Probe

<400> SEQUENCE: 103
tgaggtattt cgacaccgcc a                                                 21

<210> SEQ ID NO 104
<211> LENGTH: 23
<212> TYPE: DNA
<213> ORGANISM: Artificial Sequence
<220> FEATURE:
<223> OTHER INFORMATION: Probe

<400> SEQUENCE: 104
tgaggtattt ctacaccgcc atg                                               23

<210> SEQ ID NO 105
<211> LENGTH: 20
<212> TYPE: DNA
<213> ORGANISM: Artificial Sequence
<220> FEATURE:
<223> OTHER INFORMATION: Probe

<400> SEQUENCE: 105
tttccacacc tccgtgtccc                                                   20

<210> SEQ ID NO 106
<211> LENGTH: 19
<212> TYPE: DNA
<213> ORGANISM: Artificial Sequence
<220> FEATURE:
<223> OTHER INFORMATION: Probe

<400> SEQUENCE: 106
tctacaccgc catgtcccg                                                    19

<210> SEQ ID NO 107
<211> LENGTH: 20
<212> TYPE: DNA
<213> ORGANISM: Artificial Sequence
<220> FEATURE:
<223> OTHER INFORMATION: Probe

<400> SEQUENCE: 107
tctacacctc cgtgtcccgg                                                   20

<210> SEQ ID NO 108
<211> LENGTH: 22
<212> TYPE: DNA
<213> ORGANISM: Artificial Sequence
<220> FEATURE:
<223> OTHER INFORMATION: Probe

<400> SEQUENCE: 108
ccgcttcatc tcagtgggct ac                                                22

<210> SEQ ID NO 109
<211> LENGTH: 19
```

```
<212> TYPE: DNA
<213> ORGANISM: Artificial Sequence
<220> FEATURE:
<223> OTHER INFORMATION: Probe

<400> SEQUENCE: 109
cgcttcatca ccgtgggct                                                    19

<210> SEQ ID NO 110
<211> LENGTH: 19
<212> TYPE: DNA
<213> ORGANISM: Artificial Sequence
<220> FEATURE:
<223> OTHER INFORMATION: Probe

<400> SEQUENCE: 110
cgcttcatcg cagtgggct                                                    19

<210> SEQ ID NO 111
<211> LENGTH: 20
<212> TYPE: DNA
<213> ORGANISM: Artificial Sequence
<220> FEATURE:
<223> OTHER INFORMATION: Probe

<400> SEQUENCE: 111
tacgtggacg gcacccagtt                                                   20

<210> SEQ ID NO 112
<211> LENGTH: 20
<212> TYPE: DNA
<213> ORGANISM: Artificial Sequence
<220> FEATURE:
<223> OTHER INFORMATION: Probe

<400> SEQUENCE: 112
cgtggacgac acccagttcg                                                   20

<210> SEQ ID NO 113
<211> LENGTH: 20
<212> TYPE: DNA
<213> ORGANISM: Artificial Sequence
<220> FEATURE:
<223> OTHER INFORMATION: Probe

<400> SEQUENCE: 113
ggacgacacg ctgttcgtga                                                   20

<210> SEQ ID NO 114
<211> LENGTH: 20
<212> TYPE: DNA
<213> ORGANISM: Artificial Sequence
<220> FEATURE:
<223> OTHER INFORMATION: Probe

<400> SEQUENCE: 114
tggacgacac gcagttcgtg                                                   20

<210> SEQ ID NO 115
<211> LENGTH: 17
<212> TYPE: DNA
<213> ORGANISM: Artificial Sequence
<220> FEATURE:
<223> OTHER INFORMATION: Probe

<400> SEQUENCE: 115
```

-continued gcgacgccac gagtccg                                            17

<210> SEQ ID NO 116
<211> LENGTH: 16
<212> TYPE: DNA
<213> ORGANISM: Artificial Sequence
<220> FEATURE:
<223> OTHER INFORMATION: Probe

<400> SEQUENCE: 116
gcgacgccgc gagtcc                                             16

<210> SEQ ID NO 117
<211> LENGTH: 20
<212> TYPE: DNA
<213> ORGANISM: Artificial Sequence
<220> FEATURE:
<223> OTHER INFORMATION: Probe

<400> SEQUENCE: 117
gagtccgaga gaggagccgc                                         20

<210> SEQ ID NO 118
<211> LENGTH: 17
<212> TYPE: DNA
<213> ORGANISM: Artificial Sequence
<220> FEATURE:
<223> OTHER INFORMATION: Probe

<400> SEQUENCE: 118
ccgaggaagg agccgcg                                            17

<210> SEQ ID NO 119
<211> LENGTH: 15
<212> TYPE: DNA
<213> ORGANISM: Artificial Sequence
<220> FEATURE:
<223> OTHER INFORMATION: Probe

<400> SEQUENCE: 119
aggatggcgc cccgg                                              15

<210> SEQ ID NO 120
<211> LENGTH: 16
<212> TYPE: DNA
<213> ORGANISM: Artificial Sequence
<220> FEATURE:
<223> OTHER INFORMATION: Probe

<400> SEQUENCE: 120
ggacggagcc ccgggc                                             16

<210> SEQ ID NO 121
<211> LENGTH: 18
<212> TYPE: DNA
<213> ORGANISM: Artificial Sequence
<220> FEATURE:
<223> OTHER INFORMATION: Probe

<400> SEQUENCE: 121
cgggcgccgt ggatagag                                           18

<210> SEQ ID NO 122
<211> LENGTH: 18
<212> TYPE: DNA
<213> ORGANISM: Artificial Sequence

```
<220> FEATURE:
<223> OTHER INFORMATION: Probe

<400> SEQUENCE: 122
cgggcgccat ggatagag                                                  18

<210> SEQ ID NO 123
<211> LENGTH: 19
<212> TYPE: DNA
<213> ORGANISM: Artificial Sequence
<220> FEATURE:
<223> OTHER INFORMATION: Probe

<400> SEQUENCE: 123
ggggccggaa tattgggac                                                 19

<210> SEQ ID NO 124
<211> LENGTH: 19
<212> TYPE: DNA
<213> ORGANISM: Artificial Sequence
<220> FEATURE:
<223> OTHER INFORMATION: Probe

<400> SEQUENCE: 124
ggggccggag tattgggac                                                 19

<210> SEQ ID NO 125
<211> LENGTH: 21
<212> TYPE: DNA
<213> ORGANISM: Artificial Sequence
<220> FEATURE:
<223> OTHER INFORMATION: Probe

<400> SEQUENCE: 125
gggaccggga gacacagatc t                                              21

<210> SEQ ID NO 126
<211> LENGTH: 21
<212> TYPE: DNA
<213> ORGANISM: Artificial Sequence
<220> FEATURE:
<223> OTHER INFORMATION: Probe

<400> SEQUENCE: 126
tgggaccgga acacacagat c                                              21

<210> SEQ ID NO 127
<211> LENGTH: 22
<212> TYPE: DNA
<213> ORGANISM: Artificial Sequence
<220> FEATURE:
<223> OTHER INFORMATION: Probe

<400> SEQUENCE: 127
acacagaagt acaagcgcca gg                                             22

<210> SEQ ID NO 128
<211> LENGTH: 21
<212> TYPE: DNA
<213> ORGANISM: Artificial Sequence
<220> FEATURE:
<223> OTHER INFORMATION: Probe

<400> SEQUENCE: 128
acacggaaca tgaaggcctc c                                              21
```

<210> SEQ ID NO 129
<211> LENGTH: 24
<212> TYPE: DNA
<213> ORGANISM: Artificial Sequence
<220> FEATURE:
<223> OTHER INFORMATION: Probe

<400> SEQUENCE: 129
cacacagatc ttcaagacca acac                                             24

<210> SEQ ID NO 130
<211> LENGTH: 20
<212> TYPE: DNA
<213> ORGANISM: Artificial Sequence
<220> FEATURE:
<223> OTHER INFORMATION: Probe

<400> SEQUENCE: 130
atctgcaagg ccaaggcaca                                                  20

<210> SEQ ID NO 131
<211> LENGTH: 21
<212> TYPE: DNA
<213> ORGANISM: Artificial Sequence
<220> FEATURE:
<223> OTHER INFORMATION: Probe

<400> SEQUENCE: 131
tacaaggccc aggcacagac t                                                21

<210> SEQ ID NO 132
<211> LENGTH: 18
<212> TYPE: DNA
<213> ORGANISM: Artificial Sequence
<220> FEATURE:
<223> OTHER INFORMATION: Probe

<400> SEQUENCE: 132
acacagactg accgagag                                                    18

<210> SEQ ID NO 133
<211> LENGTH: 23
<212> TYPE: DNA
<213> ORGANISM: Artificial Sequence
<220> FEATURE:
<223> OTHER INFORMATION: Probe

<400> SEQUENCE: 133
cacacagact taccgagaga gcc                                              23

<210> SEQ ID NO 134
<211> LENGTH: 16
<212> TYPE: DNA
<213> ORGANISM: Artificial Sequence
<220> FEATURE:
<223> OTHER INFORMATION: Probe

<400> SEQUENCE: 134
gcaccgcgct ccgcta                                                      16

<210> SEQ ID NO 135
<211> LENGTH: 19
<212> TYPE: DNA
<213> ORGANISM: Artificial Sequence
<220> FEATURE:
<223> OTHER INFORMATION: Probe

```
<400> SEQUENCE: 135
cggaccctgc tccgctact                                                  19

<210> SEQ ID NO 136
<211> LENGTH: 17
<212> TYPE: DNA
<213> ORGANISM: Artificial Sequence
<220> FEATURE:
<223> OTHER INFORMATION: Probe

<400> SEQUENCE: 136
acctgcggat cgcgctc                                                    17

<210> SEQ ID NO 137
<211> LENGTH: 16
<212> TYPE: DNA
<213> ORGANISM: Artificial Sequence
<220> FEATURE:
<223> OTHER INFORMATION: Probe

<400> SEQUENCE: 137
cggaacctgc gcggct                                                     16

<210> SEQ ID NO 138
<211> LENGTH: 22
<212> TYPE: DNA
<213> ORGANISM: Artificial Sequence
<220> FEATURE:
<223> OTHER INFORMATION: Probe

<400> SEQUENCE: 138
cgggtctcac atcatccaga gg                                              22

<210> SEQ ID NO 139
<211> LENGTH: 21
<212> TYPE: DNA
<213> ORGANISM: Artificial Sequence
<220> FEATURE:
<223> OTHER INFORMATION: Probe

<400> SEQUENCE: 139
gggtctcaca ccctccagag g                                               21

<210> SEQ ID NO 140
<211> LENGTH: 23
<212> TYPE: DNA
<213> ORGANISM: Artificial Sequence
<220> FEATURE:
<223> OTHER INFORMATION: Probe

<400> SEQUENCE: 140
tcacacttgg cagacgatgt atg                                             23

<210> SEQ ID NO 141
<211> LENGTH: 22
<212> TYPE: DNA
<213> ORGANISM: Artificial Sequence
<220> FEATURE:
<223> OTHER INFORMATION: Probe

<400> SEQUENCE: 141
acaccctcca gaggatgtac gg                                              22

<210> SEQ ID NO 142
```

```
<211> LENGTH: 16
<212> TYPE: DNA
<213> ORGANISM: Artificial Sequence
<220> FEATURE:
<223> OTHER INFORMATION: Probe

<400> SEQUENCE: 142
cgacctgggg cccgac                                                   16

<210> SEQ ID NO 143
<211> LENGTH: 16
<212> TYPE: DNA
<213> ORGANISM: Artificial Sequence
<220> FEATURE:
<223> OTHER INFORMATION: Probe

<400> SEQUENCE: 143
cgacgtgggg ccggac                                                   16

<210> SEQ ID NO 144
<211> LENGTH: 19
<212> TYPE: DNA
<213> ORGANISM: Artificial Sequence
<220> FEATURE:
<223> OTHER INFORMATION: Probe

<400> SEQUENCE: 144
gggtaccacc aggacgcct                                                19

<210> SEQ ID NO 145
<211> LENGTH: 19
<212> TYPE: DNA
<213> ORGANISM: Artificial Sequence
<220> FEATURE:
<223> OTHER INFORMATION: Probe

<400> SEQUENCE: 145
cgggtatgac caggacgcc                                                19

<210> SEQ ID NO 146
<211> LENGTH: 18
<212> TYPE: DNA
<213> ORGANISM: Artificial Sequence
<220> FEATURE:
<223> OTHER INFORMATION: Probe

<400> SEQUENCE: 146
gggcatgacc agtccgcc                                                 18

<210> SEQ ID NO 147
<211> LENGTH: 20
<212> TYPE: DNA
<213> ORGANISM: Artificial Sequence
<220> FEATURE:
<223> OTHER INFORMATION: Probe

<400> SEQUENCE: 147
gcgggtataa ccagttcgcc                                               20

<210> SEQ ID NO 148
<211> LENGTH: 19
<212> TYPE: DNA
<213> ORGANISM: Artificial Sequence
<220> FEATURE:
<223> OTHER INFORMATION: Probe

<400> SEQUENCE: 148
```

```
gaggacctgc gctcctgga                                              19

<210> SEQ ID NO 149
<211> LENGTH: 19
<212> TYPE: DNA
<213> ORGANISM: Artificial Sequence
<220> FEATURE:
<223> OTHER INFORMATION: Probe

<400> SEQUENCE: 149
gaggacctga gctcctgga                                              19

<210> SEQ ID NO 150
<211> LENGTH: 16
<212> TYPE: DNA
<213> ORGANISM: Artificial Sequence
<220> FEATURE:
<223> OTHER INFORMATION: Probe

<400> SEQUENCE: 150
ggaccgccgc ggacac                                                 16

<210> SEQ ID NO 151
<211> LENGTH: 16
<212> TYPE: DNA
<213> ORGANISM: Artificial Sequence
<220> FEATURE:
<223> OTHER INFORMATION: Probe

<400> SEQUENCE: 151
ggaccgcggc ggacac                                                 16

<210> SEQ ID NO 152
<211> LENGTH: 17
<212> TYPE: DNA
<213> ORGANISM: Artificial Sequence
<220> FEATURE:
<223> OTHER INFORMATION: Probe

<400> SEQUENCE: 152
cggacacggc ggctcag                                                17

<210> SEQ ID NO 153
<211> LENGTH: 17
<212> TYPE: DNA
<213> ORGANISM: Artificial Sequence
<220> FEATURE:
<223> OTHER INFORMATION: Probe

<400> SEQUENCE: 153
cggacaccgc ggctcag                                                17

<210> SEQ ID NO 154
<211> LENGTH: 16
<212> TYPE: DNA
<213> ORGANISM: Artificial Sequence
<220> FEATURE:
<223> OTHER INFORMATION: Probe

<400> SEQUENCE: 154
ggcccgtgag gcggag                                                 16

<210> SEQ ID NO 155
<211> LENGTH: 16
<212> TYPE: DNA
```

```
<213> ORGANISM: Artificial Sequence
<220> FEATURE:
<223> OTHER INFORMATION: Probe

<400> SEQUENCE: 155
ggcccgtgtg gcggag                                                         16

<210> SEQ ID NO 156
<211> LENGTH: 20
<212> TYPE: DNA
<213> ORGANISM: Artificial Sequence
<220> FEATURE:
<223> OTHER INFORMATION: Probe

<400> SEQUENCE: 156
gcggagcagg acagagccta                                                     20

<210> SEQ ID NO 157
<211> LENGTH: 20
<212> TYPE: DNA
<213> ORGANISM: Artificial Sequence
<220> FEATURE:
<223> OTHER INFORMATION: Probe

<400> SEQUENCE: 157
gcggagcagt ggagagccta                                                     20

<210> SEQ ID NO 158
<211> LENGTH: 20
<212> TYPE: DNA
<213> ORGANISM: Artificial Sequence
<220> FEATURE:
<223> OTHER INFORMATION: Probe

<400> SEQUENCE: 158
gcggagcagc tgagagccta                                                     20

<210> SEQ ID NO 159
<211> LENGTH: 23
<212> TYPE: DNA
<213> ORGANISM: Artificial Sequence
<220> FEATURE:
<223> OTHER INFORMATION: Probe

<400> SEQUENCE: 159
agcagctgag aacctacctg gag                                                 23

<210> SEQ ID NO 160
<211> LENGTH: 23
<212> TYPE: DNA
<213> ORGANISM: Artificial Sequence
<220> FEATURE:
<223> OTHER INFORMATION: Probe

<400> SEQUENCE: 160
agcagctgag agcctacctg gag                                                 23

<210> SEQ ID NO 161
<211> LENGTH: 17
<212> TYPE: DNA
<213> ORGANISM: Artificial Sequence
<220> FEATURE:
<223> OTHER INFORMATION: Probe

<400> SEQUENCE: 161
ggagggcgag tgcgtgg                                                        17
```

```
<210> SEQ ID NO 162
<211> LENGTH: 17
<212> TYPE: DNA
<213> ORGANISM: Artificial Sequence
<220> FEATURE:
<223> OTHER INFORMATION: Probe

<400> SEQUENCE: 162
ggagggcacg tgcgtgg                                                    17

<210> SEQ ID NO 163
<211> LENGTH: 17
<212> TYPE: DNA
<213> ORGANISM: Artificial Sequence
<220> FEATURE:
<223> OTHER INFORMATION: Probe

<400> SEQUENCE: 163
ggagggcctg tgcgtgg                                                    17

<210> SEQ ID NO 164
<211> LENGTH: 18
<212> TYPE: DNA
<213> ORGANISM: Artificial Sequence
<220> FEATURE:
<223> OTHER INFORMATION: Probe

<400> SEQUENCE: 164
cgtggagtcg ctccgcag                                                   18

<210> SEQ ID NO 165
<211> LENGTH: 18
<212> TYPE: DNA
<213> ORGANISM: Artificial Sequence
<220> FEATURE:
<223> OTHER INFORMATION: Probe

<400> SEQUENCE: 165
cgtggagtgg ctccgcag                                                   18

<210> SEQ ID NO 166
<211> LENGTH: 21
<212> TYPE: DNA
<213> ORGANISM: Artificial Sequence
<220> FEATURE:
<223> OTHER INFORMATION: Probe

<400> SEQUENCE: 166
ctccgcagac acctggagaa c                                               21

<210> SEQ ID NO 167
<211> LENGTH: 21
<212> TYPE: DNA
<213> ORGANISM: Artificial Sequence
<220> FEATURE:
<223> OTHER INFORMATION: Probe

<400> SEQUENCE: 167
gctccgcaga tacctggaga a                                               21

<210> SEQ ID NO 168
<211> LENGTH: 18
<212> TYPE: DNA
<213> ORGANISM: Artificial Sequence
<220> FEATURE:
```

```
<223> OTHER INFORMATION: Probe

<400> SEQUENCE: 168
aggacaagct ggagcgcg                                          18

<210> SEQ ID NO 169
<211> LENGTH: 16
<212> TYPE: DNA
<213> ORGANISM: Artificial Sequence
<220> FEATURE:
<223> OTHER INFORMATION: Probe

<400> SEQUENCE: 169
ggacacgctg gagcgc                                            16

<210> SEQ ID NO 170
<211> LENGTH: 18
<212> TYPE: DNA
<213> ORGANISM: Artificial Sequence
<220> FEATURE:
<223> OTHER INFORMATION: Probe

<400> SEQUENCE: 170
gggagacgct gcagcgcg                                          18

<210> SEQ ID NO 171
<211> LENGTH: 25
<212> TYPE: DNA
<213> ORGANISM: Artificial Sequence
<220> FEATURE:
<223> OTHER INFORMATION: Probe

<400> SEQUENCE: 171
cttgtggcag cttaagtttg aatgt                                  25

<210> SEQ ID NO 172
<211> LENGTH: 25
<212> TYPE: DNA
<213> ORGANISM: Artificial Sequence
<220> FEATURE:
<223> OTHER INFORMATION: Probe

<400> SEQUENCE: 172
tggagtactc tacgtctgag tgtca                                  25

<210> SEQ ID NO 173
<211> LENGTH: 22
<212> TYPE: DNA
<213> ORGANISM: Artificial Sequence
<220> FEATURE:
<223> OTHER INFORMATION: Probe

<400> SEQUENCE: 173
ggagcaggtt aaacatgagt gt                                     22

<210> SEQ ID NO 174
<211> LENGTH: 23
<212> TYPE: DNA
<213> ORGANISM: Artificial Sequence
<220> FEATURE:
<223> OTHER INFORMATION: Probe

<400> SEQUENCE: 174
cctgtggcag ggtaagtata agt                                    23
```

```
<210> SEQ ID NO 175
<211> LENGTH: 23
<212> TYPE: DNA
<213> ORGANISM: Artificial Sequence
<220> FEATURE:
<223> OTHER INFORMATION: Probe

<400> SEQUENCE: 175
ttggagtact ctacgggtga gtg                                      23

<210> SEQ ID NO 176
<211> LENGTH: 20
<212> TYPE: DNA
<213> ORGANISM: Artificial Sequence
<220> FEATURE:
<223> OTHER INFORMATION: Probe

<400> SEQUENCE: 176
cctgtggcag cctaagaggg                                          20

<210> SEQ ID NO 177
<211> LENGTH: 16
<212> TYPE: DNA
<213> ORGANISM: Artificial Sequence
<220> FEATURE:
<223> OTHER INFORMATION: Probe

<400> SEQUENCE: 177
cctggagcag gcgcgg                                              16

<210> SEQ ID NO 178
<211> LENGTH: 18
<212> TYPE: DNA
<213> ORGANISM: Artificial Sequence
<220> FEATURE:
<223> OTHER INFORMATION: Probe

<400> SEQUENCE: 178
cctggaagac gagcgggc                                            18

<210> SEQ ID NO 179
<211> LENGTH: 19
<212> TYPE: DNA
<213> ORGANISM: Artificial Sequence
<220> FEATURE:
<223> OTHER INFORMATION: Probe

<400> SEQUENCE: 179
ccaggaggag aacgtgcgc                                           19

<210> SEQ ID NO 180
<211> LENGTH: 18
<212> TYPE: DNA
<213> ORGANISM: Artificial Sequence
<220> FEATURE:
<223> OTHER INFORMATION: Probe

<400> SEQUENCE: 180
cctggaagac aggcgggc                                            18

<210> SEQ ID NO 181
<211> LENGTH: 21
<212> TYPE: DNA
<213> ORGANISM: Artificial Sequence
<220> FEATURE:
<223> OTHER INFORMATION: Probe
```

```
<400> SEQUENCE: 181
cggttgctgg aaagatgcat c                                      21

<210> SEQ ID NO 182
<211> LENGTH: 27
<212> TYPE: DNA
<213> ORGANISM: Artificial Sequence
<220> FEATURE:
<223> OTHER INFORMATION: Probe

<400> SEQUENCE: 182
cggttcctgg acagatactt ctatcac                                27

<210> SEQ ID NO 183
<211> LENGTH: 24
<212> TYPE: DNA
<213> ORGANISM: Artificial Sequence
<220> FEATURE:
<223> OTHER INFORMATION: Probe

<400> SEQUENCE: 183
tgcagttcct ggaaagactc ttct                                   24

<210> SEQ ID NO 184
<211> LENGTH: 22
<212> TYPE: DNA
<213> ORGANISM: Artificial Sequence
<220> FEATURE:
<223> OTHER INFORMATION: Probe

<400> SEQUENCE: 184
cggtatctgc acagaggcat ct                                     22

<210> SEQ ID NO 185
<211> LENGTH: 19
<212> TYPE: DNA
<213> ORGANISM: Artificial Sequence
<220> FEATURE:
<223> OTHER INFORMATION: Probe

<400> SEQUENCE: 185
tgctggaaag acgcgtcca                                         19

<210> SEQ ID NO 186
<211> LENGTH: 25
<212> TYPE: DNA
<213> ORGANISM: Artificial Sequence
<220> FEATURE:
<223> OTHER INFORMATION: Probe

<400> SEQUENCE: 186
cggttactgg agagacactt ccata                                  25

<210> SEQ ID NO 187
<211> LENGTH: 21
<212> TYPE: DNA
<213> ORGANISM: Artificial Sequence
<220> FEATURE:
<223> OTHER INFORMATION: Probe

<400> SEQUENCE: 187
cggcctgatg aggagtactg g                                      21

<210> SEQ ID NO 188
<211> LENGTH: 19
```

```
<212> TYPE: DNA
<213> ORGANISM: Artificial Sequence
<220> FEATURE:
<223> OTHER INFORMATION: Probe

<400> SEQUENCE: 188
cctgtcgccg agtcctgga                                                19

<210> SEQ ID NO 189
<211> LENGTH: 20
<212> TYPE: DNA
<213> ORGANISM: Artificial Sequence
<220> FEATURE:
<223> OTHER INFORMATION: Probe

<400> SEQUENCE: 189
ggcctgatgc cgagtactgg                                               20

<210> SEQ ID NO 190
<211> LENGTH: 20
<212> TYPE: DNA
<213> ORGANISM: Artificial Sequence
<220> FEATURE:
<223> OTHER INFORMATION: Probe

<400> SEQUENCE: 190
caggaggagc tcctgcgctt                                               20

<210> SEQ ID NO 191
<211> LENGTH: 18
<212> TYPE: DNA
<213> ORGANISM: Artificial Sequence
<220> FEATURE:
<223> OTHER INFORMATION: Probe

<400> SEQUENCE: 191
gagcagaagc ggggccgg                                                 18

<210> SEQ ID NO 192
<211> LENGTH: 17
<212> TYPE: DNA
<213> ORGANISM: Artificial Sequence
<220> FEATURE:
<223> OTHER INFORMATION: Probe

<400> SEQUENCE: 192
tcctggagcg gaggcgg                                                  17

<210> SEQ ID NO 193
<211> LENGTH: 17
<212> TYPE: DNA
<213> ORGANISM: Artificial Sequence
<220> FEATURE:
<223> OTHER INFORMATION: Probe

<400> SEQUENCE: 193
gcgggccctg gtggaca                                                  17

<210> SEQ ID NO 194
<211> LENGTH: 17
<212> TYPE: DNA
<213> ORGANISM: Artificial Sequence
<220> FEATURE:
<223> OTHER INFORMATION: Probe

<400> SEQUENCE: 194
```

```
gggggagttc cgggcgg                                                    17

<210> SEQ ID NO 195
<211> LENGTH: 17
<212> TYPE: DNA
<213> ORGANISM: Artificial Sequence
<220> FEATURE:
<223> OTHER INFORMATION: Probe

<400> SEQUENCE: 195
gggggagtac cgggcgg                                                    17

<210> SEQ ID NO 196
<211> LENGTH: 20
<212> TYPE: DNA
<213> ORGANISM: Artificial Sequence
<220> FEATURE:
<223> OTHER INFORMATION: Probe

<400> SEQUENCE: 196
ggcctgacgc tgagtactgg                                                 20

<210> SEQ ID NO 197
<211> LENGTH: 20
<212> TYPE: DNA
<213> ORGANISM: Artificial Sequence
<220> FEATURE:
<223> OTHER INFORMATION: Probe

<400> SEQUENCE: 197
caatgggacg gagcgggtgc                                                 20

<210> SEQ ID NO 198
<211> LENGTH: 18
<212> TYPE: DNA
<213> ORGANISM: Artificial Sequence
<220> FEATURE:
<223> OTHER INFORMATION: Probe

<400> SEQUENCE: 198
aatgggacgg agcgggtg                                                   18

<210> SEQ ID NO 199
<211> LENGTH: 14
<212> TYPE: DNA
<213> ORGANISM: Artificial Sequence
<220> FEATURE:
<223> OTHER INFORMATION: Probe

<400> SEQUENCE: 199
gggacggagc gggt                                                       14

<210> SEQ ID NO 200
<211> LENGTH: 16
<212> TYPE: DNA
<213> ORGANISM: Artificial Sequence
<220> FEATURE:
<223> OTHER INFORMATION: Probe

<400> SEQUENCE: 200
gggggagttc cgggcg                                                     16

<210> SEQ ID NO 201
<211> LENGTH: 17
<212> TYPE: DNA
<213> ORGANISM: Artificial Sequence
```

```
<220> FEATURE:
<223> OTHER INFORMATION: Probe

<400> SEQUENCE: 201
tgggggagta ccgggcg                                                    17

<210> SEQ ID NO 202
<211> LENGTH: 22
<212> TYPE: DNA
<213> ORGANISM: Artificial Sequence
<220> FEATURE:
<223> OTHER INFORMATION: Probe

<400> SEQUENCE: 202
accaagagga gtacgtgcgc tt                                              22

<210> SEQ ID NO 203
<211> LENGTH: 18
<212> TYPE: DNA
<213> ORGANISM: Artificial Sequence
<220> FEATURE:
<223> OTHER INFORMATION: Probe

<400> SEQUENCE: 203
gcctgctgcg gagcactg                                                   18

<210> SEQ ID NO 204
<211> LENGTH: 19
<212> TYPE: DNA
<213> ORGANISM: Artificial Sequence
<220> FEATURE:
<223> OTHER INFORMATION: Probe

<400> SEQUENCE: 204
ccaggaggag ttcgtgcgc                                                  19

<210> SEQ ID NO 205
<211> LENGTH: 18
<212> TYPE: DNA
<213> ORGANISM: Artificial Sequence
<220> FEATURE:
<223> OTHER INFORMATION: Probe

<400> SEQUENCE: 205
cctggaagac gagcgggc                                                   18

<210> SEQ ID NO 206
<211> LENGTH: 18
<212> TYPE: DNA
<213> ORGANISM: Artificial Sequence
<220> FEATURE:
<223> OTHER INFORMATION: Probe

<400> SEQUENCE: 206
gcctgctgcg gagcactg                                                   18

<210> SEQ ID NO 207
<211> LENGTH: 20
<212> TYPE: DNA
<213> ORGANISM: Artificial Sequence
<220> FEATURE:
<223> OTHER INFORMATION: Probe

<400> SEQUENCE: 207
ggcctgatgc cgagtactgg                                                 20
```

```
<210> SEQ ID NO 208
<211> LENGTH: 19
<212> TYPE: DNA
<213> ORGANISM: Artificial Sequence
<220> FEATURE:
<223> OTHER INFORMATION: Probe

<400> SEQUENCE: 208
ccaggaggag aacgtgcgc                                                19

<210> SEQ ID NO 209
<211> LENGTH: 18
<212> TYPE: DNA
<213> ORGANISM: Artificial Sequence
<220> FEATURE:
<223> OTHER INFORMATION: Probe

<400> SEQUENCE: 209
cctggaagac gagcgggc                                                 18

<210> SEQ ID NO 210
<211> LENGTH: 15
<212> TYPE: DNA
<213> ORGANISM: Artificial Sequence
<220> FEATURE:
<223> OTHER INFORMATION: Probe

<400> SEQUENCE: 210
gacaggcgcg ccgcg                                                    15

<210> SEQ ID NO 211
<211> LENGTH: 17
<212> TYPE: DNA
<213> ORGANISM: Artificial Sequence
<220> FEATURE:
<223> OTHER INFORMATION: Probe

<400> SEQUENCE: 211
ctggagcaga ggcgggc                                                  17

<210> SEQ ID NO 212
<211> LENGTH: 21
<212> TYPE: DNA
<213> ORGANISM: Artificial Sequence
<220> FEATURE:
<223> OTHER INFORMATION: Probe

<400> SEQUENCE: 212
aaccaagagg agtacgtgcg c                                             21

<210> SEQ ID NO 213
<211> LENGTH: 17
<212> TYPE: DNA
<213> ORGANISM: Artificial Sequence
<220> FEATURE:
<223> OTHER INFORMATION: Probe

<400> SEQUENCE: 213
aatgggacgc agcggbt                                                  17
```

```
<210> SEQ ID NO 214
<211> LENGTH: 21
<212> TYPE: DNA
<213> ORGANISM: Artificial Sequence
<220> FEATURE:
<223> OTHER INFORMATION: Probe

<400> SEQUENCE: 214
catcctggaa gacgagcggg g                                               21
```

DNA CHIP BASED GENETIC TYPING

CROSS-REFERENCE TO RELATED APPLICATIONS

This application is the national phase of PCT application PCT/CN2003/000580 having an international filing date of Jul. 18, 2003, which claims priority from China application number 03148529.4 filed Jun. 30, 2003. The contents of these documents are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 514572001200Seqlist | Aug. 13, 2009 | 36,039 bytes |

TECHNICAL FIELD

This invention relates generally to the field of nucleic acid analysis. In particular, the invention provides a method for typing a target gene, using, inter alia, a chip comprising a support suitable for use in nucleic acid hybridization having immobilized thereon an oligonucleotide probe complementary to said target nucleotide sequence and at least one of the following oligonucleotide control probes: a positive control probe, a negative control probe, a hybridization control probe and an immobilization control probe. Oligonucleotide probes or probe arrays for typing a human leukocyte antigen (HLA) target gene are also provided.

BACKGROUND ART

Human leukocyte antigens (HLA) are encoded by HLA gene complex located on the short arm of human chromosome six. The human HLA genes are part of the major histocompatibility complex (MHC), a cluster of genes associated with tissue antigens and immune responses. Successful organ transplantation between individuals depends on the degree of acceptance, i.e., histocompatibility, between donor and recipient pairs. Antigens that cause rejection to the transplanted organ are transplantation antigens or histocompatibility antigens. There are more than twenty antigen systems related to rejection reaction in a human body. Among them, the one that can cause strong and acute rejection reaction is called major histocompatibility antigen. Its gene is a cluster of tightly connected genes, called major histocompatibility complex (MHC). It has now being proved that the immune response gene (IR gene) that controls immune response and regulating function is located in MHC. Thus, MHC not only relates to transplantation rejection but also involves widely in induction and regulation of immune response and regulation. HLA genes are located in a region of about 4000 kb located on human chromosome six, occurring about 1/3,000 of the the entire human genome. There are 224 identified HLA loci. The HLA proteins are classified, based on their structures, expression pattern, tissues distribution, and function, into three classes: HLA-I, HLA-II, and HLA-III. Within each gene locus, there are hundreds of alleles.

The proteins encoded by HLA genes play an important role in graft rejection during tissue transplantation. Successful tissue transplantation depends on achieving a degree of HLA matching between donor and recipient. Thus, HLA typing is necessary for selection of an optimally matched donor. Currently, HLA typing is routinely done in connection with many medical procedures, e.g., organ transplantation, especially bone marrow transplantation. Based on extensive polymorphism in HLA genes of the human population, the role of the proteins encoded by HLA genes in regulating immune response, and codominant expression by both the paternal and maternal genes, HLA typing is also used in predicting susceptibility to diseases, forensic identification, paternity determination, and genetic studies. Accordingly, there is a need for accurate HLA typing methods.

Different methods have been used for HLA typing. Currently, HLA genes are typed using serological methods, mixed lymphocyte culture methods (MLC), and DNA sequence-based typing methods.

Serological methods are based on reactions of sera with the HLA proteins on the surface of lymphocytes. Methods based on the principle of serological typing, such as ID-IEF and monoclonal antibody typing method, have been developed to improve specificity and shorten the testing time. Major drawbacks to serological HLA typing are the complexity of the sera, the lack of widespread availability of standard sera necessary to conduct the tests, and that only the already known HLA types, but not new polymorphisms, are detected.

In mixed lymphocyte culture (MLC) tests, lymphocytes from one individual (the "responder") are cultured with "stimulating" lymphocytes from another individual. When the stimulating cells are from unrelated persons or family members whose MHC is different from that of the responder, the untreated lymphocytes proliferate; this proliferation is an indicator for non-matching antigens from the individuals. MLC methods are not widely used for the lack of availability of typing cells and complexity of testing procedures.

DNA sequence-based HLA typing methods have been developed to overcome drawbacks with serological or mixed lymphocyte culture methods. One such method involves the use of DNA restriction fragment length polymorphism (RFLP) as a basis for HLA typing. See U.S. Pat. No. 4,582,788. Polymorphism in the length of restriction endonuclease digests generated by polymorphism in the HLA genes of the human population in combination with polymerase chain reaction (PCR) technology are used for HLA typing. However, RFLP method fails to differentiate between certain alleles that are known to exist in the population (e.g., subtypes of HLA-DR4), and thus, cannot be used to distinguish certain combinations of alleles. Moreover, its practical usefulness is limited because the procedures involved take about two weeks to complete and require use of radioactivity.

More recently, researchers have established sequence-specific oligonucleotide (SSO) probe hybridization method to perform HLA-II typing. The method entails amplifying a polymorphic region of a HLA locus using PCR, hybridizing the amplified DNA to a sequence-specific oligonucleotide probe(s), and detecting hybrids formed between the amplified DNA and the sequence-specific oligonucleotide probes. This method can identify one or two nucleotide difference between HLA alleles. The drawbacks of this method is the complexity and difficulty of making multiple equivalent membranes for hybridization or reuse of the same membrane after hybridization which currently is not automated due to the high number of alleles under investigation. Although reverse line strip typing method has been developed to improve the SSO method using an enzymatic method for generating signals for detection, the operation of this method is complicated and difficult to get desired results.

Sequence specific primer amplification (PCR-SSP) method for HLA typing utilises the specific sequence sites in PCR primer for PCR amplification of HLA type and analyzes amplified product by electrophoresis. The time required for the test using this method is only 2 to 3 hours. Mytilineos et al., Hum. Immunol., 59: 512-7 (1998). However, for an unknown sample, the method requires a lot of research for testing each specific primer. In addition, it is difficult to obtain high resolution typing for HLA subtypes.

Other DNA sequence-based HLA typing method includes PCR single strand conformation polymorphism (PCR-SSCP) and PCR fingerprinting. DNA sequence-based HLA typing method has made HLA typing more precise and also help identify more HLA alleles.

DNA chip technology has been widely used for analysing a large number of different DNA sequences or fragments simultaneously on a single DNA chip. The technique allows high-throughput, simultaneous and fast analysis of DNA fragments and requires very minute amount of the target DNA fragment. Because of the complexity of HLA genes, DNA chip can be an ideal tool for use in HLA typing. A few kits and methods have been described. See Kahiwase, Rinsho Byori Suppl. 110: 99-106 (1999); Cao et al., Rev. Immunogenet. 1: 177-208 (1999); and Guo et al., Rev. Immunogenet. 1: 220-30 (1999).

DISCLOSURE OF THE INVENTION

In one aspect, the present invention is directed to a method for typing a target gene, which method comprises: a) isolating a target cell comprising a target gene from a suitable sample and obtaining a preparation comprising a target nucleotide sequence that is at least a part of said target gene from said isolated target cell and, optionally another nucleotide sequence not related to said target gene; b) providing a chip comprising a support suitable for use in nucleic acid hybridization having immobilized thereon an oligonucleotide probe complementary to said target nucleotide sequence and at least one of the following oligonucleotide control probes: a positive control probe, a negative control probe, a hybridization control probe and an immobilization control probe; and c) hybridizing said preparation obtained in step a) to said chip provided in step b) and assessing hybridization between said target nucleotide sequence and/or said another nucleotide sequence and said control probes comprised on said chip to determine the type of said target gene.

In another aspect, the present invention is directed to an oligonucleotide probe for typing a HLA target gene comprising a nucleotide sequence that: a) hybridizes, under high stringency, with a target HLA nucleotide sequence, or a complementary strand thereof, that is set forth in Table 1; or b) has at least 90% identity to a target HLA nucleotide sequence comprising a nucleotide sequence, or a complementary strand thereof, that is set forth in Table 1.

In still another aspect, the present invention is directed to an array of oligonucleotide probes immobilized on a support for typing a HLA target gene, which array comprises a support suitable for use in nucleic acid hybridization having immobilized thereon a plurality of oligonucleotide probes, at least one of said probes comprising a nucleotide sequence that: a) hybridizes, under high stringency, with a target HLA nucleotide sequence, or a complementary strand thereof, that is set forth in Table 1; or b) has at least 90% identity to a target HLA nucleotide sequence comprising a nucleotide sequence, or a complementary strand thereof, that is set forth in Table 1.

MODES OF CARRYING OUT THE INVENTION

Figure 1:
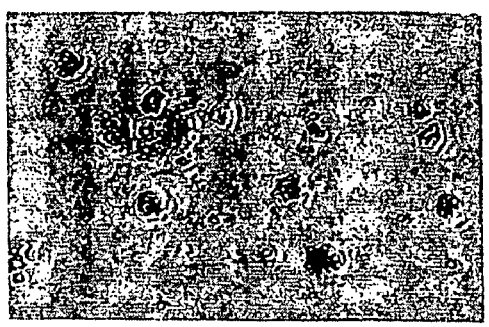
FIG. 1 illustrates the results that the leukocyte was captured by the magnetic microbead.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "primer" refers to an oligonucleotide that hybridizes to a target sequence, typically to prime the nucleic acid in the amplification process.

As used herein, "probe" refers to an oligonucleotide that hybridizes to a target sequence, typically to facilitate its detection. The term "target sequence" refers to a nucleic acid sequence to which the probe specifically binds. Unlike a primer that is used to prime the target nucleic acid in the amplification process, a probe need not be extended to amplify target sequence using a polymerase enzyme. However, it will be apparent to those skilled in the art that probes and primers are structurally similar or identical in many cases.

As used herein, "positive control probe" refers to a probe that hybridizes to conserved or consensus sequences of a group (or family) of target sequences. As used herein, "negative control probe" refers to a probe that comprises a single or multiple basepair change(s) when compared to the positive control probe. Preferably, a negative control probe comprises a single basepair change when compared to the positive control probe. Another exemplary negative control probe is a homologous sequence from an origin that is different from an origin from which the target sequence is derived. In one specific example, two positive control probes, i.e., a stronger one and a weaker one, and a single negative control probe can be used together. The stronger positive control probe and the negative control probe are used to assess overall hybridization efficacy. The weaker positive control probe is used to assess hybridization signals of the testing probes, i.e., the non-control probes whose hybridization is to be assessed. For example, a ratio between hybridization signals of the testing probes and hybridization signals of the weaker positive control probe can be used to derive a range to assess the strength of hybridization of the testing probes.

As used herein, "hybridization control probe" refers to probe(s) that is used to assess overall hybridization efficacy independent of the hybridization between the testing probe and the target sequence. For example, if the target sequence is a HLA sequence, a hybridization control probe can be a sequence unrelated to any HLA sequence, preferably from an origin different from which the target HLA target sequence is derived. The hybridization control probe can be modified with a $NH_2$ group and be applied (or immobilized) to a chip surface in a same or similar concentration and/or procedure through which other probes, including the testing probes, are applied (or immobilized) to the chip surface. Another labeled probe, e.g., Hexachloro fluorescein (HEX), labeled probe, that is complementary to the hybridization control probe can be added in the overall hybridization solution in a concentration or ratio that is compatible to the concentration or ratio of other probes. Other fluoresceins also can be used here. In this way, the overall hybridization process can be monitored. The hybridization control probe can also be used in guiding or determining locations of probes on the chip surface.

As used herein, "immobilization control probe" refers to probe(s) that is used to assess immobilization process. An immobilization control probe does not participate in any hybridization reactions. In one example, one end of the immobilization control probe is modified, e.g., with a $NH_2$ group, to facilitate its immobilization on a chip surface, and the other end of the immobilization control probe is labeled with a detectable label, e.g., HEX.

As used herein, "HEX" means Hexachloro fluorescein, one of the Fluoresceins.

As used herein, "complementary" means that two nucleic acid sequences have at least 50% sequence identity. Preferably, the two nucleic acid sequences have at least 60%, 70,%, 80%, 90%, 95%, 96%, 97%, 98%, 99% or 100% sequence identity. "Complementary" also means that two nucleic acid sequences can hybridize under low, middle and/or high stringency condition(s).

As used herein, "substantially complementary" means that two nucleic acid sequences have at least 90% sequence identity. Preferably, the two nucleic acid sequences have at least 95%, 96%, 97%, 98%, 99% or 100% sequence identity. Alternatively, "substantially complementary" means that two nucleic acid sequences can hybridize under high stringency condition(s).

As used herein, "two perfectly matched nucleotide sequences" refers to a nucleic acid duplex wherein the two nucleotide strands match according to the Watson-Crick basepair principle, i.e., A-T and C-G pairs in DNA:DNA duplex and A-U and C-G pairs in DNA:RNA or RNA:RNA duplex, and there is no deletions or additions in either of the sequences in the duplex.

As used herein: "stringency of hybridization" in determining percentage mismatch is as follows:
 1) high stringency: 0.1× SSPE, 0.1% SDS, 65° C.;
 2) medium stringency: 0.2× SSPE, 0.1% SDS, 50° C. (also referred to as moderate stringency); and
 3) low stringency: 1.0× SSPE, 0.1% SDS, 50° C.

It is understood that equivalent stringencies may be achieved using alternative buffers, salts and temperatures (See generally, Ausubel (Ed.) *Current Protocols in Molecular Biology*, 2.9A. *Southern Blotting*, 2.9B. *Dot and Slot Blotting of DNA and* 2.10. *Hybridization Analysis of DNA Blots*, John Wiley & Sons, Inc. (2000)).

As used herein, "melting temperature" ("Tm") refers to the midpoint of the temperature range over which nucleic acid duplex, i.e., DNA:DNA, DNA:RNA and RNA:RNA, is denatured. The Tm of the probe herein means the Tm of the hybridized probe.

As used herein, "assessing" refers to quantitative and/or qualitative determination of the hybrid formed between the probe and the target nucleotide sequence, e.g., obtaining an absolute value for the amount or concentration of the hybrid, and also of obtaining an index, ratio, percentage, visual or other value indicative of the level of hybridization. Assessment may be direct or indirect, and the chemical species actually detected need not be the hybrid itself but may, for example, be a derivative thereof, reduction or disappearance of the probe and/or the target nucleotide sequence, or some further substance.

As used herein, "magnetic substance" refers to any substance that has the properties of a magnet, pertaining to a magnet or to magnetism, producing, caused by, or operating by means of, magnetism.

As used herein, "magnetizable substance" refers to any substance that has the property of being interacted with the field of a magnet, and hence, when suspended or placed freely in a magnetic field, of inducing magnetization and producing a magnetic moment. Examples of magnetizable substances include, but are not limited to, paramagnetic, ferromagnetic and ferrimagnetic substances.

As used herein, "paramagnetic substance" refers to the substances where the individual atoms, ions or molecules possess a permanent magnetic dipole moment. In the absence of an external magnetic field, the atomic dipoles point in random directions and there is no resultant magnetization of the substances as a whole in any direction. This random orientation is the result of thermal agitation within the substance. When an external magnetic field is applied, the atomic dipoles tend to orient themselves parallel to the field, since this is the state of lower energy than antiparallel position. This gives a net magnetization parallel to the field and a positive contribution to the susceptibility. Further details on "paramagnetic substance" or "paramagnetism" can be found in various literatures, e.g., at Page 169-page 171, Chapter 6, in "Electricity and Magnetism" by B. I Bleaney and B. Bleaney, Oxford, 1975.

As used herein, "ferromagnetic substance" refers to the substances that are distinguished by very large (positive) values of susceptibility, and are dependent on the applied magnetic field strength. In addition, ferromagnetic substances may possess a magnetic moment even in the absence of the applied magnetic field, and the retention of magnetization in zero field is known as "remanence". Further details on "ferromagnetic substance" or "ferromagnetism" can be found in various literatures, e.g., at Page 171-page 174, Chapter 6, in "Electricity and Magnetism" by B. I Bleaney and B. Bleaney, Oxford, 1975.

As used herein, "ferrimagnetic substance" refers to the substances that show spontaneous magnetization, remanence, and other properties similar to ordinary ferromagnetic materials, but the spontaneous moment does not correspond to the value expected for full parallel alignment of the (magnetic) dipoles in the substance. Further details on "ferrimagnetic substance" or "ferrimagnetism" can be found in various literatures, e.g., at Page 519-524, Chapter 16, in "Electricity and Magnetism" by B. I Bleaney and B. Bleaney, Oxford, 1975.

As used herein, "metal oxide particle" refers to any oxide of a metal in a particle form. Certain metal oxide particles have paramagnetic or super-paramagnetic properties. "Paramagnetic particle" is defined as a particle which is susceptible to the application of external magnetic fields, yet is unable to maintain a permanent magnetic domain. In other words, "paramagnetic particle" may also be defined as a particle that is made from or made of "paramagnetic substances". Non-limiting examples of paramagnetic particles include certain metal oxide particles, e.g., $Fe_3O_4$ particles, metal alloy particles, e.g., CoTaZr particles.

As used herein, "the sample, e.g., the whole blood, is fresh" means that the sample has been obtained or isolated from its natural source within about 12 hours. Preferably, the sample has been obtained or isolated from its natural source within about 10, 5, 4, 3, 2 hours, 1 hour, 30, 20, 10, 5, 2 minutes or 1 minute.

As used herein, "the sample, e.g., the whole blood, is low-temperature conserved" means that the sample has been conserved at a temperature about at or below 0° C.

B. Methods for Typing a Target Gene

In one aspect, the present invention is directed to a method for typing a target gene, which method comprises: a) isolating a target cell comprising a target gene from a suitable sample and obtaining a preparation comprising a target nucleotide sequence that is at least a part of said target gene from said isolated target cell and, optionally another nucleotide sequence not related to said target gene; b) providing a chip comprising a support suitable for use in nucleic acid hybridization having immobilized thereon an oligonucleotide probe complementary to said target nucleotide sequence and at least one of the following oligonucleotide control probes: a positive control probe, a negative control probe, a hybridization control probe and an immobilization control probe; and c) hybridizing said preparation obtained in step a) to said chip provided in step b) and assessing hybridization between said target nucleotide sequence and/or said another nucleotide sequence and said control probes comprised on said chip to determine the type of said target gene.

The present methods can be used to type a target gene from any target cell, e.g., a leukocyte. Other exemplary target cells include animal cells, plant cells, fungus cells, bacterium cells, recombinant cells and cultured cells.

The present methods can be used to type any target gene, e.g., a human leukocyte antigen (HLA).

Any suitable sample, e.g., blood, saliva, hair and a human tissue that comprises a human nucleic acid, can be used in the present methods. In one example, the blood sample is serum, plasma or whole blood. In another example, the blood sample is fresh or low-temperature conserved whole blood.

The target cell can be isolated from a suitable sample using any suitable methods. For example, the target cell can be isolated from the suitable sample using a magnetic microbead. Preferably, the magnetic microbead has a diameter ranging from about 5 μm to about 200 μm.

The magnetic microbeads can be prepared by any suitable methods. For example, the methods disclosed in CN 01/109870.8 or WO02/075309 can be used. Any suitable magnetizable substance can be used to prepare the magnetic microbeads useful in the present methods. No-limiting examples of the magnetizable substances include ferrimagnetic substance, ferromagnetic substance, paramagnetic substance or superparamagnetic substances. In a specific embodiment, the magnetic microbeads comprise a paramagnetic substance, e.g., a paramagnetic metal oxide composition. Preferably, the paramagnetic metal oxide composition is a transition metal oxide or an alloy thereof. Any suitable transition metals can be used, such as iron, nickel, copper, cobalt, manganese, tantalum (Ta), zinc and zirconium (Zr). In a preferred embodiment, the metal oxide composition is $Fe_3O_4$ or $Fe_2O_3$. In another example, the magnetizable substance used in the magnetic microbeads comprises a metal composition. Preferably, the metal composition is a transition metal composition or an alloy thereof such as iron, nickel, copper, cobalt, manganese, tantalum, zirconium and cobalt-tantalum-zirconium (CoTaZr) alloy.

The magnetic microbeads may be prepared from the available primary beads, from raw materials or front metal oxides that are encapsulated by monomers which when crosslinked form rigid, polymeric coatings as disclosed in U.S. Pat. No. 5,834,121. As used herein, "rigid" refers to a polymeric coating that is cross linked to the extent that the polymeric coating stabilizes the metal oxide particle within the coating (i.e. the coating essentially does not swell or dissolve) so that the particle remains enclosed therein. As used herein, "microporous" refers to a resinous polymeric matrix that swells or expands in polar organic solvent. As used herein, "load" is used to mean the capacity of the bead for attachment sites useful for functionalization or derivatization.

Suitable substances which may be incorporated as magnetizable materials, for example, include iron oxides such as magnetite, ferrites of manganese, cobalt, and nickel, hematite and various alloys. Magnetite is the preferred metal oxide. Frequently, metal salts are taught to be converted to metal oxides then either coated with a polymer or adsorbed into a bead comprising a thermoplastic polymer resin having reducing groups thereon. When starting with metal oxide particles to obtain a hydrophobic primary bead, it is necessary to provide a rigid coating of a thermoplastic polymer derived from vinyl monomers, preferably a cross-linked polystyrene that is capable of binding or being bound by a microporous matrix. Magnetic particles may be formed by methods known in the art, e.g., procedures shown in Vandenberge et al., *J. of Magnetism and Magnetic Materials*, 15-18:1117-18 (1980); Matijevic, *Acc. Chem. Res.*, 14:22-29 (1981); and U.S. Pat. Nos. 5,091,206; 4,774,265; 4,554,088; and 4,421,660. Examples of primary beads that may be used in this invention are shown in U.S. Pat. Nos. 5,395,688; 5,318,797; 5,283,079; 5,232,7892; 5,091,206; 4,965,007; 4,774,265; 4,654,267; 4,490,436; 4,336,173; and 4,421,660. Or, primary beads may be obtained commercially from available hydrophobic or hydrophilic beads that meet the starting requirements of size, sufficient stability of the polymeric coating to swell in solvents to retain the paramagnetic particle, and ability to adsorb or absorb the vinyl monomer used to form the enmeshing matrix network. Preferably, the primary bead is a hydrophobic, polystyrene encapsulated, paramagnetic bead. Such polystyrene paramagnetic beads are available from Dynal, Inc. (Lake Success, N.Y.), Rhone Poulonc (France), and SINTEF (Trondheim, Norway). The use of toner particles or of magnetic particles having a first coating of an unstable polymer which are further encapsulated to produce an exterior rigid polymeric coating is also contemplated.

The preparation of the target nucleotide sequence can comprise a nucleic acid amplification step. The target nucleotide sequence can be obtained via nucleic acid amplification directly from the isolated target cell. Alternatively, the target nucleotide sequence can be obtained via nucleic acid amplification using a nucleic acid template isolated from the isolated target cell. Any suitable nucleic acid amplification step can be used, e.g., polymerase chain reaction (PCR), ligase chain reaction (LCR), nucleic acid sequence-based amplification (NASBA), strand displacement amplification (SDA) and transcription-medicated amplification (TMA). Preferable the TMA is driven by a T7 promoter.

Also preferably, the PCR is asymmetrical PCR. The two primers used in the asymmetrical PCR can have any suitable ratio, e.g., a ratio ranging from about 1:5 to about 1:200. The two primers used in the asymmetrical PCR can have same or different Tm values. For example, the difference between the Tm value of the two primers used in the asymmetrical PCR can range from about 1° C. to about 20° C. In another example, three primers are used in the asymmetrical PCR, two of the primers having same of similar Tm value and the difference between the Tm value of the two primers and that of the third primer ranges from about 1° C. to about 20° C. The primers can be straight-chain primers or comprise a hairpin structure. A single or multiple annealing temperatures can be used in the PCR. For example, the difference between the annealing temperatures can range from about 1° C. to about 20° C.

The target nucleotide sequence obtained in step a) of the present methods can be single-, double- or triple-stranded. Preferably, the target nucleotide sequence obtained in step a) is single-stranded DNA or RNA. The target nucleotide sequence obtained in step a) of the present methods can be a positive or negative strand. Preferably, the single-stranded DNA or RNA is positive or negative strand. A labeled target nucleotide sequence can be obtained in step a). Preferably, the labeled target nucleotide sequence comprises a fluorescent or biotin label. Also preferably, the another nucleotide sequence can be complementary to the positive control probe, the negative control probe or the hybridization control probe comprised on the chip.

The probes comprised on the chip can be positive-stranded or negative-stranded probes. The probes comprised on the chip can be modified. Exemplary probe modifications include 5'-$NH_2$ modification, 5'-SH modification, 5'-polyT (or A, C or G) modification, 5'-biotin modification, 3'-$NH_2$ modification, 3'-SH modification, 3'-polyT (or A, C or G) modification and 3'-biotin modification.

The chip used in the present methods can comprise any suitable types or number of probes. For example, the chip can comprise 1-500 different types of probes. In another example, the chip can comprise multiple arrays of probes and each array comprises 1-400 different types of probes.

The probes can be immobilized on the chip at any suitable temperature, e.g., a temperature ranging from about 40° C. to about 100° C. The chip can be modified. Exemplary chip modifications include CHO, $NH_2$, poly-lysine, SH, BSA, streptavidin, agarose gel and polyacrylamide gel modification.

The sequence, purity or terminal modification of the probes can be assessed. Preferably, the sequence, purity or terminal modification of the probes is assessed via DHPLC.

Any suitable copies or number of a probe can be immobilized on the chip. For example, multiple copies of a probe, e.g., 1-10 copies of a probe, can be immobilized on the chip.

The multiple copies or number of probes can be immobilized on the chip according to any suitable patterns. For example, the multiple copies or number of probes can be immobilized adjacently or separately on the chip. Preferably, the multiple copies of a positive control probe are immobilized on the chip and the variations in the length and sequence of the immobilized positive control probes, when hybridized with the target nucleotide sequence or the another nucleotide sequence in the preparation provided in step a), create a group of hybridization signals having strong-to-weak or weak-to-strong orderly magnitude.

Any suitable positive control probes can be used in the present methods. Preferably, the positive control probe is complementary to a portion of the target nucleotide sequence, a nucleotide sequence amplified synchronically with the target nucleotide sequence or a synthetic nucleotide sequence.

Any suitable negative control probes can be used in the present methods. Preferably, the negative control probe has about 1-3 basepair mismatches when compared to the positive control probe.

Any suitable hybridization control probes can be used in the present methods. Preferably, the hybridization control probe is complementary to a synthetic nucleotide sequence not related to the target gene. More preferably, the hybridization control probe is complementary to a synthetic labeled nucleotide sequence or has about 1-2 basepair mismatches when compared to the synthetic labeled nucleotide sequence.

Any suitable immobilization control probes can be used in the present methods. Preferably, the immobilization control probe does not generate any hybridization signal Generally, the immobilization control probe is an internal control probe for the quality control of the chemical modified slides, spot process, immobilization procedure, etc. It does not hybridize with the target nucleic acids. In one specific embodiment, one end of the immobilization control probe is chemically modified and the other end of the immobilization control probe has a detectable label.

The chip used in the present methods can comprise any, some or all of the positive control probe, the negative control probe, the hybridization control probe and the immobilization control probe. In one specific embodiment, the chip comprises a positive control probe, a negative control probe, a hybridization control probe and an immobilization control probe. The positive control probe, the negative control probe, the hybridization control probe and/or the immobilization control probe can be immobilized on the chip in any suitable pattern. For example, the positive control probe, the negative control probe, the hybridization control probe and the immobilization control probe can be immobilized on the four corners of the chip, in the center of the chip or have any suitable orderly or random immobilization pattern.

The hybridization reaction in step c) can be conducted in any suitable hybridization solution, e.g., a hybridization solution comprising sodium chloride/sodium citrate (SSC) and a surfactant. The hybridization solution can comprise any suitable concentration of SSC, e.g., from about 3× to about 10× SSC. Any suitable surfactant, e.g., sodium dodecyl sulfate (SDS), Triton ×100 and sodium lauryl sarcosine (SLS), can be used. The hybridization solution can comprise any suitable concentration of surfactant, e.g., a concentration ranging from about 0.05% (w/w) to about 5% (w/w).

The hybridization reaction in step c) can be conducted at any suitable temperature, e.g., at a temperature ranging from about 42° C. to about 70° C.

The present methods can further comprise a washing step after the hybridization reaction. Any suitable washing solution can be used. For example, the washing step can be conducted in a washing solution comprising a surfactant having a concentration ranging from about 0% (w/w) to about 2% (w/w). The washing step can be conducted for any suitable time, e.g., for a time ranging from about 5 minutes to about 30 minutes.

The immobilization efficiency of various probes can be assessed by any usitable methods. For example, the immobilization efficiency can be assessed by analyzing a signal from the immobilization control probe. The immobilization control probe can carry a detectable label, e.g., a fluorescence molecule.

The overall hybridization efficiency, including hybridization involving the oligonucleotide probe complementary to the target nucleotide sequence and various control probes, can be assessed by any suitable methods. For example, the overall hybridization efficiency can be assessed by analyzing the hybridization between the hybridization control probe and a labeled synthetic nucleotide sequence not related to the target gene.

The overall hybridization specificity, including hybridization involving the oligonucleotide probe complementary to the target nucleotide sequence and various control probes, can be assessed by any suitable methods. For example, the hybridization specificity can be assessed by analyzing the ratio between the hybridization signal involving the positive control probe and the hybridization signal involving the negative control probe, and the ratio between the hybridization signal involving the positive hybridization control probe and the hybridization signal involving the negative hybridization control probe, and increased ratios indicating the increased hybridization specificity.

Positive signal(s) can be determined based on any suitable criteria. For example, in hybridizations involving a group of closely related probes, a positive signal(s) can be determined based on the following criteria: a) the ratio of the hybridization signal over background noise is more than 3; b) the ratio of the hybridization signal over a relevant positive control probe hybridization signal is within a predetermined range; c) comparing hybridization signals of all probes giving positive signals based on the steps of a) and b), or hybridization signals of two probes giving two strongest hybridization signals when only one probe giving positive signal based on the steps of a) and b), to determine whether the signal is positive or negative; and d) there are 2 or less than 2 positive signals involving the group of closely related probes.

The group of closely related probes can be based on any suitable criteria. For example, a group of probes designed to assess variation at a particular genetic locus can be used as a group of closely related probes. The variation to be assessed can be single or multiple basepair change(s). Normally, the basepair change(s) are located within the length of a probe, e.g., within 20 bps.

The predetermined range as described in the above b) can be different for different probes. The range can be obtained through empirical studies. For example, the range can be obtained by conducting multiple, e.g., hundreds, hybridization experiments using know, standard targets and/or probes.

The present methods can be used to type any target gene. For example, the present methods can be used to type a HLA gene using an oligonucleotide probe that is complementary to the target HLA gene. Preferably, the oligonucleotide probe comprises a nucleotide sequence that: a) hybridizes, under high stringency, with a target HLA nucleotide sequence, or a complementary strand thereof, that is set forth in Table 1; or b) has at least 90% identity to a target HLA nucleotide sequence comprising a nucleotide sequence, or a complementary strand thereof, that is set forth in Table 1. Also preferably, the oligonucleotide probe comprises a nucleotide sequence, or a complementary strand thereof, that is set forth in Table 1. The chip can comprise some or all nucleotide sequences, or a complementary strand thereof, that are set forth in Table 1.

C. Oligonucleotide Probes and Probe Arrays for Typing a HLA Target Gene

In another aspect, the present invention is directed to an oligonucleotide probe for typing a HLA target gene comprising a nucleotide sequence that: a) hybridizes, under high stringency, with a target HLA nucleotide sequence, or a complementary strand thereof, that is set forth in Table 1; or b) has at least 90% identity to a target HLA nucleotide sequence comprising a nucleotide sequence, or a complementary strand thereof, that is set forth in Table 1. The oligonucleotide probe can comprise DNA, RNA, PNA or a derivative thereof. Preferably, the probe comprises a nucleotide sequence, or a complementary strand thereof, that is set forth in Table 1. The probe can be labeled. Exemplary labels include a chemical, an enzymatic, an immunogenic, a radioactive, a fluorescent, a luminescent and a FRET label.

The oligonucleotide probes can be produced by any suitable method. For example, the probes can be chemically synthesized (See generally, Ausubel (Ed.) *Current Protocols in Molecular Biology*, 2.11. *Synthesis and purification of oligonucleotides*, John Wiley & Sons, Inc. (2000)), isolated from a natural source, produced by recombinant methods or a combination thereof Synthetic oligonucleotides can also be prepared by using the triester method of Matteucci et al., *J. Am. Chem. Soc.*, 3:3185-3191 (1981). Alternatively, automated synthesis may be preferred, for example, on a Applied Biosynthesis DNA synthesizer using cyanoethyl phosphoramidite chemistry. Preferably, the probes are chemically synthesized.

Suitable bases for preparing the oligonucleotide probes of the present invention may be selected from naturally occurring nucleotide bases such as adenine, cytosine, guanine, uracil, and thymine. It may also be selected from nonnaturally occurring or "synthetic" nucleotide bases such as 8-oxo-guanine, 6-mercaptoguanine, 4-acetylcytidine, 5-(carboxyhydroxyethyl) uridine, 2'-O-methylcytidine, 5-carboxymethylamino-methyl-2-thiouridine, 5-carboxymethylaminomethyl uridine, dihydrouridine, 2'-O-methylpseudouridine, beta-D-galactosylqueosine, 2'-Omethylguanosine, inosine, $N^6$-isopentenyladenosine, 1-methyladenosine, 1-methylpseudouridine, 1-methylguanosine, 1-methylaminomethylinosine, 2,2-dimethylguanosine, 2-methyladenosine, 2-methylguanosine, 3-methylcytidine, 5-methylcytidine, $N^6$-methyladenosine, 7-methylguanosine, 5-methylaminomethyluridine, 5-methoxyaminomethyl-2-thiouridine, beta-D-mannosylqueosine, 5-methoxycarbonylmethyluridine, 5-methoxyuridine, 2-methylthio-$N^6$-isopentenyladenosine, N-((9-beta-D-ribofuranosyl-2-methylthiopurine-6-yl)carbamoyl)threonine, N-((9-beta-D-ribofuranosylpurine-6-yl) N-methylcarbamoyl) threonine, uridine-5-oxyacetic acid methylester uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9-beta-D-ribofuranosylpurine-6-yl) carbamoyl) threonine, 2'-O-methyl-5-methyluridine, 2'-O-methyluridine, wybutosine, and 3-(3-amino-3-carboxypropyl) uridine.

Likewise, chemical analogs of oligonucleotides (e.g., oligonucleotides in which the phosphodiester bonds have been modified, e.g., to the methylphosphonate, the phosphotriester, the phosphorothioate, the phosphorodithioate, or the phosphoramidate) may also be employed. Protection from degradation can be achieved by use of a "3'-end cap" strategy by which nuclease-resistant linkages are substituted for phosphodiester linkages at the 3' end of the oligonucleotide (Shaw et al., Nucleic Acids Res., 19:747 (1991)). Phosphoramidates, phosphorothioates, and methylphosphonate linkages all function adequately in this manner. More extensive modification of the phosphodiester backbone has been shown to impart stability and may allow for enhanced affinity and increased cellular permeation of oligonucleotides (Milligan et al., J. Med. Chem., 36:1923 (1993)). Many different chemical strategies have been employed to replace the entire phosphodiester backbone with novel linkages. Backbone analogues include phosphorothioate, phosphorodithioate, methylphosphonate, phosphoramidate, boranophosphate, phosphotriester, formacetal, 3'-thioformacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene (methylimino) (MMI) or methyleneoxy (methylimino) (MOMI) linkages. Phosphorothioate and methylphosphonate-modified oligonucleotides are particularly preferred due to their availability through automated oligonucleotide synthesis. The oligonucleotide may be a "peptide nucleic acid" such as described by (Milligan et al., J. Med. Chem., 36:1923 (1993)). The only requirement is that the oligonucleotide probe should possess a sequence at least a portion of which is capable of binding to a portion of the sequence of a target DNA molecule.

Hybridization probes can be of any suitable length. There is no lower or upper limits to the length of the probe, as long as the probe hybridizes to the HLA target nucleic acids and functions effectively as a probe (e.g., facilitates detection). The probes of the present invention can be as short as 50, 40, 30, 20, 15, or 10 nucleotides, or shorter. Likewise, the probes can be as long as 20, 40, 50, 60, 75, 100 or 200 nucleotides, or longer, e.g., to the full length of the HLA target sequence. Generally, the probes will have at least 14 nucleotides, preferably at least 18 nucleotides, and more preferably at least 20 to 30 nucleotides of either of the complementary target nucleic acid strands and does not contain any hairpin secondary structures. In specific embodiments, the probe can have a length of at least 30 nucleotides or at least 50 nucleotides. If there is to be complete complementarity, i.e., if the strand contains a sequence identical to that of the probe, the duplex will be relatively stable under even stringent conditions and the probes may be short, i.e., in the range of about 10-30 base pairs. If some degree of mismatch is expected in the probe, i.e., if it is suspected that the probe would hybridize to a variant region, or to a group of sequences such as all species within a specific genus, the probe may be of greater length (i.e., 15-40 bases) to balance the effect of the mismatch(es).

The probe need not span the entire HLA target gene. Any subset of the target region that has the potential to specifically identify HLA target or allele can be used. Consequently, the nucleic acid probe may hybridize to as few as 8 nucleotides of the target region. Further, fragments of the probes may be used so long as they are sufficiently characteristic of the HLA target gene to be typed.

The probe should be able to hybridize with a HLA target nucleotide sequence that is at least 8 nucleotides in length under low stringency. Preferably, the probe hybridizes with a a HLA target nucleotide sequence under middle or high stringency.

In still another aspect, the present invention is directed to an array of oligonucleotide probes immobilized on a support for typing a HLA target gene, which array comprises a support suitable for use in nucleic acid hybridization having immobilized thereon a plurality of oligonucleotide probes, at least one of said probes comprising a nucleotide sequence that: a) hybridizes, under high stringency, with a target HLA nucleotide sequence, or a complementary strand thereof, that is set forth in Table 1; or b) has at least 90% identity to a target HLA nucleotide sequence comprising a nucleotide sequence, or a complementary strand thereof, that is set forth in Table 1.

The plurality of probes can comprise DNA, RNA, PNA or a derivative thereof. At least one or some of the probes can comprise a nucleotide sequence, or a complementary strand thereof, that is set forth in Table 1. Preferably, probe arrays comprise all of the nucleotide sequences, or a complementary strand thereof, that are set forth in Table 1. At least one, some or all of the probes can be labeled. Exemplary labels include a chemical, an enzymatic, an immunogenic, a radioactive, a fluorescent, a luminescent and a FRET label. Any suitable support, e.g., a silicon, a plastic, a glass, a ceramic, a rubber, and a polymer surface, can be used.

D. Assay Formats

Immobilization of Probes

The present methods, probes and probe arrays can be used in solution. Preferably, it is conducted in chip format, e.g., by using the probe(s) immobilized on a solid support.

The probes can be immobilized on any suitable surface, preferably, a solid support, such as silicon, plastic, glass, ceramic, rubber, or polymer surface. The probe may also be immobilized in a 3-dimensional porous gel substrate, e.g., Packard HydroGel chip (Broude et al., *Nucleic Acids Res.*, 29(19):E92 (2001)).

For an array-based assay, the probes are preferably immobilized to a solid support such as a "biochip". The solid support may be biological, nonbiological, organic, inorganic, or a combination of any of these, existing as particles, strands, precipitates, gels, sheets, tubing, spheres, containers, capillaries, pads, slices, films, plates, slides, etc.

A microarray biochip containing a library of probes can be prepared by a number of well known approaches including, for example, light-directed methods, such as VLSIPS™ described in U.S. Pat. Nos. 5,143,854, 5,384,261 or 5,561,071; bead based methods such as described in U.S. Pat. No. 5,541,061; and pin based methods such as detailed in U.S. Pat. No. 5,288,514. U.S. Pat. No. 5,556,752, which details the preparation of a library of different double stranded probes as a microarray using the VLSIPS™, is also suitable for preparing a library of hairpin probes in a microarray.

Flow channel methods, such as described in U.S. Pat. Nos. 5,677,195 and 5,384,261, can be used to prepare a microarray biochip having a variety of different probes. In this case, certain activated regions of the substrate are mechanically separated from other regions when the probes are delivered through a flow channel to the support. A detailed description of the flow channel method can be found in U.S. Pat. No. 5,556,752, including the use of protective coating wetting facilitators to enhance the directed channeling of liquids though designated flow paths.

Spotting methods also can be used to prepare a microarray biochip with a variety of probes immobilized thereon. In this case, reactants are delivered by directly depositing relatively small quantities in selected regions of the support. In some steps, of course, the entire support surface can be sprayed or otherwise coated with a particular solution. In particular formats, a dispenser moves from region to region, depositing only as much probe or other reagent as necessary at each stop. Typical dispensers include micropipettes, nanopipettes, inkjet type cartridges and pins to deliver the probe containing solution or other fluid to the support and, optionally, a robotic system to control the position of these delivery devices with respect to the support. In other formats, the dispenser includes a series of tubes or multiple well trays, a manifold, and an array of delivery devices so that various reagents can be delivered to the reaction regions simultaneously. Spotting methods are well known in the art and include, for example, those described in U.S. Pat. Nos. 5,288,514, 5,312,233 and 6,024,138. In some cases, a combination of flow channels and "spotting" on predefined regions of the support also can be used to prepare microarray biochips with immobilized probes.

A solid support for immobilizing probes is preferably flat, but may take on alternative surface configurations. For example, the solid support may contain raised or depressed regions on which probe synthesis takes place or where probes are attached. In some embodiments, the solid support can be chosen to provide appropriate light-absorbing characteristics. For example, the support may be a polymerized Langmuir Blodgett film, glass or functionalized glass, Si, Ge, GaAs, GaP, $SiO_2$, $SiN_4$, modified silicon, or any one of a variety of gels or polymers such as (poly)tetrafluoroethylene, (poly)vinylidenedifluoride, polystyrene, polycarbonate, or combinations thereof. Other suitable solid support materials will be readily apparent to those of skill in the art.

The surface of the solid support can contain reactive groups, which include carboxyl, amino, hydroxyl, thiol, or the like, suitable for conjugating to a reactive group associated with an oligonucleotide or a nucleic acid. Preferably, the surface is optically transparent and will have surface Si—OH functionalities, such as those found on silica surfaces.

The probes can be attached to the support by chemical or physical means such as through ionic, covalent or other forces well known in the art. Immobilization of nucleic acids and oligonucleotides can be achieved by any means well known in the art (see, e.g., Dattagupta et al., Analytical Biochemistry, 177:85-89 (1989); Saiki et al., Proc. Natl. Acad Sci. USA, 86:6230-6234 (1989); and Gravitt et al., J. Clin. Micro., 36:3020-3027 (1998)).

The probes can be attached to a support by means of a spacer molecule, e.g., as described in U.S. Pat. No. 5,556,752 to Lockhart et al., to provide space between the double stranded portion of the probe as may be helpful in hybridization assays. A spacer molecule typically comprises between 6-50 atoms in length and includes a surface attaching portion that attaches to the support. Attachment to the support can be accomplished by carbon-carbon bonds using, for example, supports having (poly)trifluorochloroethylene surfaces, or preferably, by siloxane bonds (using, for example, glass or silicon oxide as the solid support). Siloxane bonding can be formed by reacting the support with trichlorosilyl or trialkoxysilyl groups of the spacer. Aminoalkylsilanes and hydroxyalkylsilanes, bis(2-hydroxyethyl)-aminopropyltriethoxysilane, 2-hydroxyethylaminopropyltriethoxysilane, aminopropyltriethoxysilane or hydroxypropyltriethoxysilane are useful are surface attaching groups.

The spacer can also include an extended portion or longer chain portion that is attached to the surface-attaching portion of the probe. For example, amines, hydroxyl, thiol, and carboxyl groups are suitable for attaching the extended portion of the spacer to the surface-attaching portion. The extended portion of the spacer can be any of a variety of molecules which are inert to any subsequent conditions for polymer synthesis. These longer chain portions will typically be aryl acetylene, ethylene glycol oligomers containing 2-14 monomer units, diamines, diacids, amino acids, peptides, or combinations thereof.

In some embodiments, the extended portion of the spacer is a polynucleotide or the entire spacer can be a polynucleotide. The extended portion of the spacer also can be constructed of polyethyleneglycols, polynucleotides, alkylene, polyalcohol, polyester, polyamine, polyphosphodiester and combinations thereof. Additionally, for use in synthesis of probes, the spacer can have a protecting group attached to a functional group (e.g., hydroxyl, amino or carboxylic acid) on the distal or terminal end of the spacer (opposite the solid support). After deprotection and coupling, the distal end can be covalently bound to an oligomer or probe.

The present method can be used to analyze a single sample with a single probe at a time. Preferably, the method is conducted in high-throughput format. For example, a plurality of samples can be analyzed with a single probe simultaneously, or a single sample can be analyzed using a plurality of probes simultaneously. More preferably, a plurality of samples can be analyzed using a plurality of probes simultaneously.

Hybridization Conditions

Hybridization can be carried out under any suitable technique known in the art. It will be apparent to those skilled in the art that hybridization conditions can be altered to increase or decrease the degree of hybridization, the level of specificity of the hybridization, and the background level of non-specific binding (i.e., by altering hybridization or wash salt concentrations or temperatures). The hybridization between the probe and the target nucleotide sequence can be carried out under any suitable stringencies, including high, middle or low stringency. Typically, hybridizations will be performed under conditions of high stringency.

Hybridization between the probe and target nucleic acids can be homogenous, e.g., typical conditions used in molecular beacons (Tyagi S. et al., Nature Biotechnology, 14:303-308 (1996); and U.S. Pat. No. 6,150,097) and in hybridization protection assay (Gen-Probe, Inc) (U.S. Pat. No. 6,004,745), or heterogeneous (typical conditions used in different type of nitrocellulose based hybridization and those used in magnetic bead based hybridization).

The target polynucleotide sequence may be detected by hybridization with an oligonucleotide probe that forms a stable hybrid with that of the target sequence under high to low stringency hybridization and wash conditions. An advantage of detection by hybridization is that, depending on the probes used, additional specificity is possible. If it is expected that the probes will be completely complementary (i.e., about 99% or greater) to the target sequence, high stringency conditions will be used. If some mismatching is expected, for example, if variant strains are expected with the result that the probe will not be completely complementary, the stringency of hybridization may be lessened. However, conditions are selected to minimize or eliminate nonspecific hybridization.

Conditions those affect hybridization and those select against nonspecific hybridization are known in the art (Molecular Cloning A Laboratory Manual, second edition, J. Sambrook, E. Fritsch, T. Maniatis, Cold Spring Harbor Laboratory Press, 1989). Generally, lower salt concentration and higher temperature increase the stringency of hybridization. For example, in general, stringent hybridization conditions include incubation in solutions that contain approximately 0.1×SSC, 0.1% SDS, at about 65° C. incubation/wash temperature. Middle stringent conditions are incubation in solutions that contain approximately 1-2×SSC, 0.1% SDS and about 50° C.-65° C. incubation/wash temperature. The low stringency conditions are 2×SSC and about 30° C.-50° C.

An alternate method of hybridization and washing is first to carry out a low stringency hybridization (5×SSPE, 0.5% SDS) followed by a high stringency wash in the presence of 3M tetramethyl-ammonium chloride (TMAC). The effect of the TMAC is to equalize the relative binding of A-T and G-C base pairs so that the efficiency of hybridization at a given temperature corresponds more closely to the length of the polynucleotide. Using TMAC, it is possible to vary the temperature of the wash to achieve the level of stringency desired (Wood et al., *Proc. Natl. Acad. Sci. USA*, 82:1585-1588 (1985)).

A hybridization solution may contain 25% formamide, 5×SSC, S×Denhardt's solution, 100 µg/ml of single stranded DNA, 5% dextran sulfate, or other reagents known to be useful for probe hybridization.

Detection of the Hybrid

Detection of hybridization between the probe and the target HLA nucleic acids can be carried out by any method known in the art, e.g., labeling the probe, the secondary probe, the target nucleic acids or some combination thereof, and are suitable for purposes of the present invention. Alternatively, the hybrid may be detected by mass spectroscopy in the absence of detectable label (e.g., U.S. Pat. No. 6,300,076).

The detectable label is a moiety that can be detected either directly or indirectly after the hybridization. In other words, a detectable label has a measurable physical property (e.g., fluorescence or absorbance) or is participant in an enzyme reaction. Using direct labeling, the target nucleotide sequence or the probe is labeled, and the formation of the hybrid is assessed by detecting the label in the hybrid. Using indirect labeling, a secondary probe is labeled, and the formation of the hybrid is assessed by the detection of a secondary hybrid formed between the secondary probe and the original hybrid.

Methods of labeling probes or nucleic acids are well known in the art. Suitable labels include fluorophores, chromophores, luminophores, radioactive isotopes, electron dense reagents, FRET (fluorescence resonance energy transfer), enzymes and ligands having specific binding partners. Particularly useful labels are enzymatically active groups such as enzymes (Wisdom, *Clin. Chem.*, 22:1243 (1976)); enzyme substrates (British Pat. No. 1,548,741); coenzymes (U.S. Pat. Nos. 4,230,797 and 4,238,565) and enzyme inhibitors (U.S. Pat. No. 4,134,792); fluorescers (Soini and Hemmila, *Clin. Chem.*, 25:353 (1979)); chromophores including phycobiliproteins, luminescers such as chemiluminescers and bioluminescers (Gorus and Schram, *Clin. Chem.*, 25:512 (1979) and ibid, 1531); specifically bindable ligands, i.e., protein binding ligands; antigens; and residues comprising radioisotopes such as $^3H$, $^{35}S$, $^{32}P$, $^{125}I$, and $^{14}C$. Such labels are detected on the basis of their own physical properties (e.g., fluorescers, chromophores and radioisotopes) or their reactive or binding properties (e.g., antibodies, enzymes, substrates, coenzymes and inhibitors). Ligand labels are also useful for solid phase capture of the oligonucleotide probe (i.e., capture probes). Exemplary labels include biotin (detectable by binding to labeled avidin or streptavidin) and enzymes, such as horseradish peroxidase or alkaline phosphatase (detectable by addition of enzyme substrates to produce a colored reaction product).

For example, a radioisotope-labeled probe or target nucleic acid can be detected by autoradiography. Alternatively, the probe or the target nucleic acid labeled with a fluorescent moiety can detected by fluorimetry, as is known in the art. A hapten or ligand (e.g., biotin) labeled nucleic acid can be detected by adding an antibody or an antibody pigment to the hapten or a protein that binds the labeled ligand (e.g., avidin).

As a further alternative, the probe or nucleic acid may be labeled with a moiety that requires additional reagents to detect the hybridization. If the label is an enzyme, the labeled nucleic acid, e.g., DNA, is ultimately placed in a suitable medium to determine the extent of catalysis. For example, a cofactor-labeled nucleic acid can be detected by adding the enzyme for which the label is a cofactor and a substrate for the enzyme. Thus, if the enzyme is a phosphatase, the medium can contain nitrophenyl phosphate and one can monitor the amount of nitrophenol generated by observing the color. If the enzyme is a beta-galactosidase, the medium can contain o-nitro-phenyl-D-galacto-pyranoside, which also liberates nitrophenol. Exemplary examples of the latter include, but are not limited to, beta-galactosidase, alkaline phosphatase, papain and peroxidase. For in situ hybridization studies, the final product of the substrate is preferably water insoluble. Other labels, e.g., dyes, will be evident to one having ordinary skill in the art.

The label can be linked directly to the DNA binding ligand, e.g., acridine dyes, phenanthridines, phenazines, furocoumarins, phenothiazines and quinolines, by direct chemical linkage such as involving covalent bonds, or by indirect linkage such as by the incorporation of the label in a microcapsule or liposome, which in turn is linked to the binding ligand. Methods by which the label is linked to a DNA binding ligand such as an intercalator compound are well known in the art and any convenient method can be used. Representative intercalating agents include mono- or bis-azido aminoalkyl methidium or ethidium compounds, ethidium monoazide ethidium diazide, ethidium dimer azide (Mitchell et al., *J. Am. Chem. Soc.*, 104:4265 (1982))), 4-azido-7-chloroquinoline, 2-azidofluorene, 4'-aminomethyl-4,5'-dimethylangelicin, 4'-aminomethyl-trioxsalen (4'aminomethyl-4,5',8-trimethyl-psoralen), 3-carboxy-5- or -8-amino- or -hydroxy-psoralen. A specific nucleic acid binding azido compound has been described by Forster et al., *Nucleic Acid Res.*, 13:745 (1985). Other useful photoreactable intercalators are the furocoumarins which form (2+2) cycloadducts with pyrimidine residues. Alkylating agents also can be used as the DNA binding ligand, including, for example, bis-chloroethylamines and epoxides or aziridines, e.g., aflatoxins, polycyclic hydrocarbon epoxides, mitomycin and norphillin A. Particularly useful photoreactive forms of intercalating agents are the azido-intercalators. Their reactive nitrenes are readily generated at long wavelength ultraviolet or visible light and the nitrenes of arylazides prefer insertion reactions over their rearrangement products (White et al., *Meth. Enzymol.*, 46:644 (1977)).

The probe may also be modified for use in a specific format such as the addition of 10-100 T residues for reverse dot blot or the conjugation to bovine serum albumin or immobilization onto magnetic beads.

When detecting hybridization by an indirect detection method, a detectably labeled second probe(s) can be added after initial hybridization between the probe and the target or during hybridization of the probe and the target. Optionally, the hybridization conditions may be modified after addition of the secondary probe. After hybridization, unhybridized secondary probe can be separated from the initial probe, for example, by washing if the initial probe is immobilized on a solid support. In the case of a solid support, detection of label bound to locations on the support indicates hybridization of a target nucleotide sequence in the sample to the probe.

The detectably labeled secondary probe can be a specific probe. Alternatively, the detectably labeled probe can be a degenerate probe, e.g., a mixture of sequences such as whole genomic DNA essentially as described in U.S. Pat. No. 5,348, 855. In the latter case, labeling can be accomplished with intercalating dyes if the secondary probe contains double stranded DNA. Preferred DNA-binding ligands are intercalator compounds such as those described above.

A secondary probe also can be a library of random nucleotide probe sequences. The length of a secondary probe should be decided in view of the length and composition of the primary probe or the target nucleotide sequence on the solid support that is to be detected by the secondary probe.

Such a probe library is preferably provided with a 3' or 5' end labeled with photoactivatable reagent and the other end loaded with a detection reagent such as a fluorophore, enzyme, dye, luminophore, or other detectably known moiety.

The particular sequence used in making the labeled nucleic acid can be varied. Thus, for example, an amino-substituted psoralen can first be photochemically coupled with a nucleic acid, the product having pendant amino groups by which it can be coupled to the label, i.e., labeling is carried out by photochemically reacting a DNA binding ligand with the nucleic acid in the test sample. Alternatively, the psoralen can first be coupled to a label such as an enzyme and then to the nucleic acid.

Advantageously, the DNA binding ligand is first combined with label chemically and thereafter combined with the nucleic acid probe. For example, since biotin carries a carboxyl group, it can be combined with a furocoumarin by way of amide or ester formation without interfering with the photochemical reactivity of the furocoumarin or the biological activity of the biotin. Aminomethylangelicin, psoralen and phenanthridium derivatives can similarly be linked to a label, as can phenanthridium halides and derivatives thereof such as aminopropyl methidium chloride (Hertzberg et al, *J. Amer. Chem. Soc.*, 104:313 (1982)). Alternatively, a bifunctional reagent such as dithiobis succinimidyl propionate or 1,4-butanediol diglycidyl ether can be used directly to couple the DNA binding ligand to the label where the reactants have alkyl amino residues, again in a known manner with regard to solvents, proportions and reaction conditions. Certain bifunctional reagents, possibly glutaraldehyde may not be suitable because, while they couple, they may modify nucleic acid and thus interfere with the assay. Routine precautions can be taken to prevent such difficulties.

Also advantageously, the DNA binding ligand can be linked to the label by a spacer, which includes a chain of up to about 40 atoms, preferably about 2 to 20 atoms, including, but not limited to, carbon, oxygen, nitrogen and sulfur. Such spacer can be the polyfunctional radical of a member including, but not limited to, peptide, hydrocarbon, polyalcohol, polyether, polyamine, polyimine and carbohydrate, e.g., -glycyl-glycyl-glycyl- or other oligopeptide, carbonyl dipeptides, and omega-amino-alkane-carbonyl radical or the like. Sugar, polyethylene oxide radicals, glyceryl, pentaerythritol, and like radicals also can serve as spacers. Spacers can be directly linked to the nucleic acid-binding ligand and/or the label, or the linkages may include a divalent radical of a coupler such as dithiobis succinimidyl propionate, 1,4-butanediol diglycidyl ether, a diisocyanate, carbodiimide, glyoxal, glutaraldehyde, or the like.

Secondary probe for indirect detection of hybridization can be also detected by energy transfer such as in the "beacon probe" method described by Tyagi and Kramer, *Nature Biotech.*, 14:303-309 (1996) or U.S. Pat. Nos. 5,119,801 and 5,312,728 to Lizardi et al. Any FRET detection system known in the art can be used in the present method. For example, the AlphaScreen™ system can be used. AlphaScreen technology is an "Amplified Luminescent Proximity Homogeneous Assay" method. Upon illumination with laser light at 680 nm, a photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity of the donor bead, by virtue of a biological interaction, the singlet-state oxygen molecules reacts with chemiluminescent groups in the acceptor beads, which immediately transfer energy to fluorescent acceptors in the same bead. These fluorescent acceptors shift the emission wavelength to 520-620 nm. The whole reaction has a 0.3 second half-life of decay, so measurement can take place in time-resolved mode. Other exemplary FRET donor/acceptor pairs include Fluorescein (donor) and tetramethylrhodamine (acceptor) with an effective distance of 55 Å; IAEDANS (donor) and Fluorescein (acceptor) with an effective distance of 46 Å; and Fluorescein (donor) and QSY-7 dye (acceptor) with an effective distance of 61 Å(Molecular Probes).

Quantitative assays for nucleic acid detection also can be performed according to the present invention. The amount of secondary probe bound to a microarray spot can be measured and can be related to the amount of nucleic acid target which is in the sample. Dilutions of the sample can be used along with controls containing known amount of the target nucleic acid. The precise conditions for performing these steps will be apparent to one skilled in the art. In microarray analysis, the detectable label can be visualized or assessed by placing the probe array next to x-ray film or phosphoimagers to identify the sites where the probe has bound. Fluorescence can be detected by way of a charge-coupled device (CCD) or laser scanning.

Test Samples

Any suitable samples, including samples of human, animal, or environmental (e.g., soil or water) origin, can be analyzed using the present method. Test samples can include body fluids, such as urine, blood, semen, cerebrospinal fluid, pus, amniotic fluid, tears, or semisolid or fluid discharge, e.g., sputum, saliva, lung aspirate, vaginal or urethral discharge, stool or solid tissue samples, such as a biopsy or chorionic villi specimens. Test samples also include samples collected with swabs from the skin, genitalia, or throat.

Test samples can be processed to isolate nucleic acid by a variety of means well known in the art (See generally, Ausubel (Ed.) *Current Protocols in Molecular Biology*, 2. *Preparation and Analysis of DNA* and 4. *Preparation and Analysis of RNA*, John Wiley & Sons, Inc. (2000)). It will be apparent to those skilled in the art that target nucleic acids can be RNA or DNA that may be in form of direct sample or purified nucleic acid or amplicons.

Purified nucleic acids can be extracted from the aforementioned samples and may be measured spectrophotometrically or by other instrument for the purity. For those skilled in the art of nucleic acid amplification, amplicons are obtained as end products by various amplification methods such as PCR (Polymerase Chain Reaction, U.S. Pat. Nos. 4,683,195, 4,683,202, 4,800,159 and 4,965,188), NASBA (Nucleic Acid Sequence Based Amplification, U.S. Pat. No. 5,130,238), TMA (Transcription Mediated Amplification) (Kwoh et al., *Proc. Natl. Acad Sci., USA*, 86:1173-1177 (1989)), SDA (Strand Displacement Amplification, described by Walker et al., U.S. Pat. No. 5,270,184), tSDA (thermophilic Strand Displacement Amplification (U.S. Pat. No. 5,648,211 and Euro. Pat. No. EP 0 684315), SSSR (Self-Sustained Sequence Replication) (U.S. Pat. No. 6,156,508).

In a specific embodiment, a sample of human origin is assayed. In yet another specific embodiment, a sputum, urine, blood, tissue section, food, soil or water sample is assayed.

Kits

The present probes can be packaged in a kit format, preferably with an instruction for using the probes to detect a target gene. The components of the kit are packaged together in a common container, typically including written instructions for performing selected specific embodiments of the methods disclosed herein. Components for detection methods, as described herein, may optionally be included in the kit, for example, a second probe, and/or reagents and means for carrying out label detection (e.g., radiolabel, enzyme substrates, antibodies, etc., and the like).

E. Exemplary Embodiments

The exemplary embodiments described herein provide methods for typing a target gene, for example HLA typing, using a DNA chip. Such typing can be used in construction of human bone marrow stem cell donor library and human umbilical cord blood stem cell library, organ transplantation testing, bone marrow transplantation testing, studies in autoimmune disease, virus infection, and cancer research, studies in predicting susceptibility to diseases, forensic identification, paternity determinations, and human genetics studies, etc.

In one aspect, the exemplary embodiments provide a method for tying a target gene, which method comprises: a) isolating a target cell comprising a target gene from a suitable sample and obtaining a preparation comprising a target nucleotide sequence that is at least a part of said target gene from said isolated target cell and, optionally another nucleotide sequence not related to said target gene; b) providing a chip comprising a support suitable for use in nucleic acid hybridization having immobilized thereon an oligonucleotide probe complementary to said target nucleotide sequence and at least one of the following oligonucleotide control probes: a positive control probe, a negative control probe, a hybridization control probe and an immobilization control probe; and c) hybridizing said preparation obtained in step a) to said chip provided in step b) and assessing hybridization between said target nucleotide sequence and/or said another nucleotide sequence and said control probes comprised on said chip to determine the type of said target gene. In some embodiments, the target gene is a HLA gene, e.g., a HLA class I or class II gene.

In one embodiment, the preparation of the target nucleotide sequence is obtained by isolating leukocyte from whole blood using magnetic microbeads, isolating nucleic acid from the leukocyte or using the leukocyte directly for a target gene amplification to obtain the preparation of the target nucleotide sequence, wherein the target nucleotide sequence is a single-stranded DNA or RNA comprising a fluorescent or biotin label.

The present embodiment provides an improved method for preparation of the target nucleotide sequence. The prior methods for preparation of the target nucleotide sequence require the steps of purifying DNA from whole blood before amplification of the target nucleotide sequence by PCR and purifying and denaturing the PCR product for later hybridization. See, U.S. Pat. No. 5,702,885. The present method for preparation of the target nucleotide sequence permits using leukocyte isolated from whole blood with magnetic microbeads directly as PCT template or nucleic acid isolated from the leukocyte for nucleic acid amplification to obtain single-stranded DNA or RNA comprising a fluorescent or biotin label. The labeled DNA or RNA can be used for hybridization without being further purified.

In this embodiment, the single-stranded DNA or RNA can be obtained using asymmetrical PCR. The PCR amplification process can be conventional asymmetrical PCR using unequal amount of primers. The primers can be straight-chain primers or have a hairpin structure. The primers used in the asymmetrical PCR can have same or different Tm values. The difference between the Tm value of two or more primers used in the asymmetrical PCR can range from about 1° C. to about 20° C. One of the primers can have a lower Tm value to allow amplification of double-stranded product. The other primer can have a higher Tm value to allow amplification of single-stranded DNA after obtaining certain amount of double stranded-DNA. The single-stranded target nucleotide sequence generated by this PCR amplification process can be used directly for hybridization without further purification. Example 1 demonstrated that the single-stranded HLA target nucleotide sequence obtained by this method could be used for DNA chip hybridization without further purification.

Alternatively, single-stranded RNA can be obtained by transcription-medicated amplification (TMA) method. A primer comprising a T7 promoter can be included for amplification and a single-stranded RNA can be synthesized by T7 RNA polymerase. Using single-stranded DNA or RNA for hybridization avoids the step of purifying and denaturing the PCR amplified product and problem of weak or loss of signal while using double-stranded DNA for hybridization.

In this embodiment, the magnetic microbeads is prepared by the methods disclosed in CN Pat. NO. 01134861.5.

The method disclosed herein for the preparation of a target nucleotide sequence can be used for fast nucleic acid sample preparation and for active biochip operation in order to construct a micro-total analysis system (or lab-on-a-chip).

Figure 2:
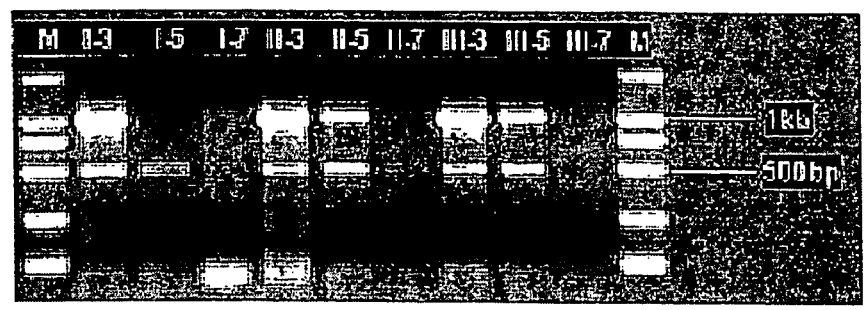
FIG. 2 illustrates PCR results from leukocytes isolated using three different types of magnetic microbead.

The PCR system and process is further detailed in Example 1. The PCR amplification product is shown in FIG. 1 and FIG. 2.

In another embodiment, the chip of the invention is constructed by designing oligonucleotide probes according to the published HLA allele gene sequences, and immobilizing the probes on chemically modified surface of the chip.

In this embodiment, the probes are designed according to published HLA allele gene sequence for middle-level resolution HLA typing and immobilized on chemically modified support of the chip. The probes can be positive-stranded or negative-stranded probes. The probes can have about 10-30 nucleotides. The HLA allele gene sequence can be first analyzed by a sequence analysis software to identify single nucleotide polymorphism (SNP) site, and probe sequence covering the SNP site is designed based on the required Tm value. Examples of the probes used for the invention are shown in Table 1.

In this embodiment, the probes can be immobilized on the support of the chip at a temperature higher than room temperature to increase immobilization efficiency. Higher immobilization efficiency saves the amount of probes to be used and reduces the cost of chip construction. The prior methods for immobilizing probes use room temperature or close to room temperature. The present embodiment uses higher temperature to immobilize probes having $NH_2$ modification at one end of the probe because the reaction between $NH_2$ group and CHO group to form —NH—CO— bond is more efficient at a higher temperature.

In another embodiment, a method is provided for assessing the quality of the probes, such as purity and the terminal modification, via DHPLC. Terminal modification efficiency is an important indication for the quality of the probes. DHPLC can separate terminally modified and unmodified probes and thus can be used for quality control of the probes. An example of using DHPLC for assessing terminal NH2 modification of probes is shown in Table 2. DHPLC can also be used to assess nucleotide mutations or deletions in the probes.

In another embodiment, a method comprising hybridizing the preparation comprising the target nucleotide sequence to the chip, washing the chip with a solution, scanning the chip after hybridization for signals, and assessing hybridization between the target nucleotide sequence and the probes immobilized on the chip to determine the type of the target gene.

In this embodiment, hybridization condition and washing condition that give strong signal and minimize possibility of false positive signal are selected. The probes used for the invention are selected from sequences according to human HLA allele gene sequence provided from the Twelfth International Conference of Histocompatibility (fti.ebi.ac.uk) and cloned standard HLA allele gene. The cloned standard HLA allele genes were sequenced and many sequences did not match sequences provided by the Twelfth International Conference of Histocompatibility. A HLA allele gene library was constructed for designing probes of the invention.

In another embodiment, a series of control probes and a pattern of probe arrangement shown in Table 3 are provided to assess the quality of the chip and reliability of the result from the hybridization process. The arrangement of probes shown in Table 3 can be used for typing a target gene, including but not limited to HLA typing. Multiple copies (for example, 1-10 copies) of a probe can be immobilized on the chip. The multiple copies of the probe can be immobilized adjacently or separately on the chip. One to ten copies of a positive control probe can be immobilized on the chip and the variations in the length and sequence of the immobilized positive control probes, when hybridized with the target nucleotide sequence, create a group of hybridization signals having strong-to-weak or weak-to-strong orderly magnitude. The negative control probe has about 1-3 basepair mismatches when compared to the positive control probe. The positive or the negative control probe can be complementary to a portion of the target nucleotide sequence, a nucleotide sequence amplified synchronically with the target nucleotide sequence, or a synthetic nucleotide sequence. The hybridization control probe can be complementary to a synthetic nucleotide sequence not related to the target gene. The hybridization control probe can be complementary to a synthetic labeled nucleotide sequence or has about 1-2 basepair mismatches when compared to the synthetic labeled nucleotide sequence. The immobilization control probe is a probe that is chemically modified at one end (for example, $NH_2$ modified) and has a detectable label (for example, fluorescent label) at the other end. The immobilization control probe is complementary to a synthetic nucleotide sequence not related to the target gene. The positive control probe, the negative control probe, the hybridization control probe, and the immobilization control probe can be immobilized on the four corners of the chip, in the center of the chip, or have any suitable orderly or random immobilization pattern. This pattern arrangement for the control probes can be used, but not limited to, for HLA typing.

In another embodiment, a method for data analysis is provided for assessing the hybridization signal which can be used for typing any target gene, including but not limited to typing a HLA gene. The method includes assessment of the immobilization efficiency, the overall hybridization efficiency, the hybridization specificity, and the positive signal and the negative signal. The overall hybridization efficiency can be assessed by analyzing a signal from the immobilization control probe, analyzing the hybridization between the hybridization control probe and a labeled synthetic nucleotide sequence not related to the target gene, and analyzing the hybridization signal involving the positive control probe and the negative control probe. The hybridization specificity can be assessed by analyzing the ratio between the hybridization signal involving the positive control probe and the hybridization signal involving the negative control probe, and the ratio between the hybridization signal involving the positive hybridization control probe and the hybridization signal involving the negative hybridization control probe, and increased ratios indicating the increased hybridization specificity. In hybridizations involving a group of closely related probes, a positive signal(s) can be determined based on the following criteria: a) the ratio of the hybridization signal over background noise is more than 3; b) the ratio of the hybridization signal over a relevant positive control probe hybridization signal is within a predetermined range; c) comparing hybridization signals of all probes giving positive signals based on the steps of a) and b), or hybridization signals of two probes giving two strongest hybridization signals when only one probe giving positive signal based on the steps of a) and b), to determine whether the signal is positive or negative; and d) there are 2 or less than 2 positive signals involving the group of closely related probes.

After the hybridization, the chip can be scanned and the data can be analyzed. A target gene type, for example, a HLA gene, can be determined using a data analyzing software.

F. Example

Example 1

To isolate a target cell for typing a target HLA gene, 5 ul of whole blood with anti-agglutination agent in ACD (23 mM citric acid, 80 mM glucose, and 45 mM sodium citrate) were mixed gently with 20 ul magnetic beads (which is in TE buffer pH6.0 at 15 mg/ml) in a 1.5 ml Eppendorf tube on rotating shaker for 10 seconds and allowed to settle for 3 minutes. The magnetic beads were then immobilized by a magnetic stand and the supernatant was discarded. The magnetic beads were washed two times with PBS. After wash, the magnetic beads were resuspended in 100 ul TE buffer, 5 ul of the resuspended magnetic beads were used as template for PCT amplification. PCR was carried out in 25 ul of PCT reaction solution made by mixing 2.5 ul of 10× buffer, 0.5 ul of 10 mM dNTP, 0.5 ul of 1 mM Cy5 labeled dCTP, 0.5 ul of 100 ng/ul template DNA, 0.5 ul of 1 uM upstream primer, 2.5 ul of 10 uM downstream primer, 0.5 ul of 5 U/ul Taq polymerase, and sterile double distilled water to make final reaction volume to 25 ul. The PCT amplification process included 3 minutes at 96° C.; twenty six cycles of 25 second at 96° C., 45 second at 71° C., and 30 second at 72° C.; nine cycles of 25 second at 96° C., 60 second at 68° C., and 120 second at 72° C.; followed by 8 minutes at 72° C.

After the PCT amplification, the reaction product may be analyzed by 1.2% agarose gel electrophoresis. The reaction product may be used directly for the following hybridization reaction without being analyzed. µ

To perform hybridization, 5 ul of PCT reaction product, after being mixed with 3 ul hybridization solution, were incubated at 98° C. for 5 minutes. The hybridization reaction was then carried out at 65° C. for 1 hour to allow hybridization of PCT reaction product with probes immobilized on a DNA chip. After hybridization, unreacted PCT reaction product on the chip was washed off using deionized water. The chip was further washed for 10 minutes at 45° C. in washing buffer and rinsed in deionized water. The chip was then dried.

Figure 3:
FIG. 3 illustrates PCR results from leukocytes isolated using same magnetic microbead.
Figure 4:
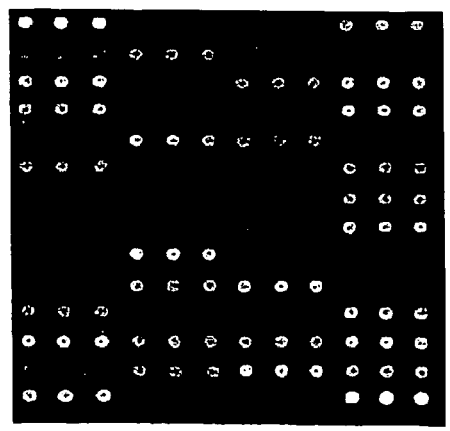
FIG. 4 illustrates hybridization signals on a chip comprising 144 probes.

The hybridized chip was scanned by a specialized scanner and a hybridization pattern was obtained (FIG. 3). The hybridization pattern was analyzed using a specialized software to generate a database. The database was analyzed and genetic typing of the target gene was obtained.

Example 2

To determine quality of probes, two oligonucleotide probes (PBH_0303019 and PBH_0301119) that had NH2 modification at one end at 10 uM in H2O, were applied to WAVE®

Figure 5A:
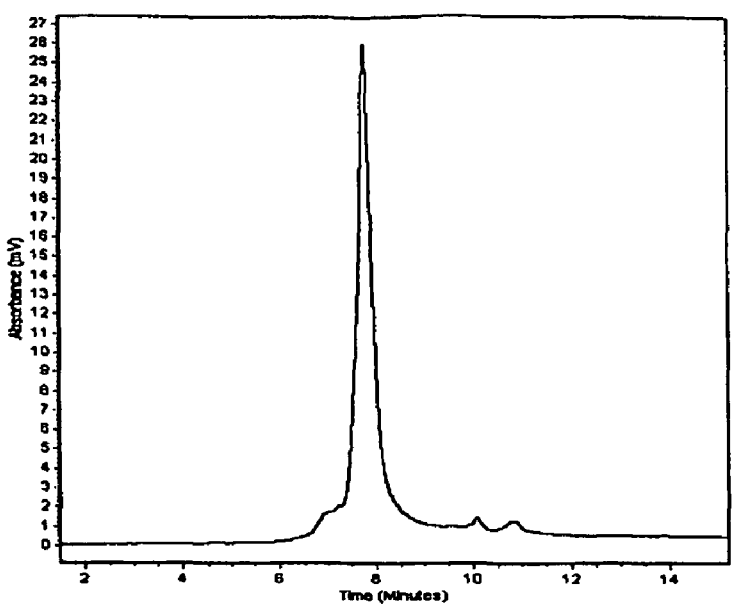
FIG. 5 illustrates DHPLC analysis of two probes: PBH__0303019 and PBH__0301119.
Figure 5B:
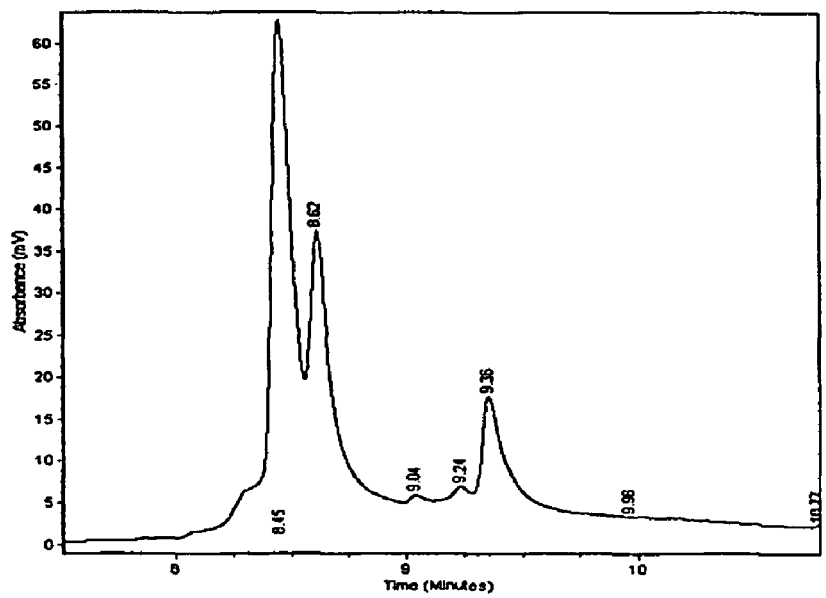
Figure 6A:
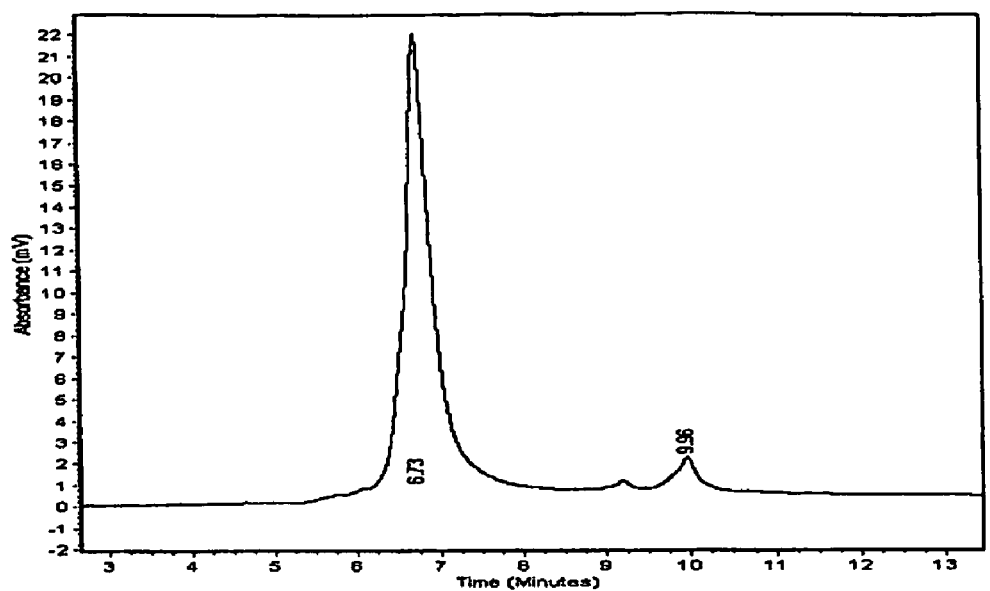
FIG. 6 illustrates DHPLC analysis of four types of probes: 6a. a very pure probe; 6b. a probe with little impurities; 6c. a probe with high percent impurities; 6d. a very poor probe with very high percent impurities.
Figure 6B:
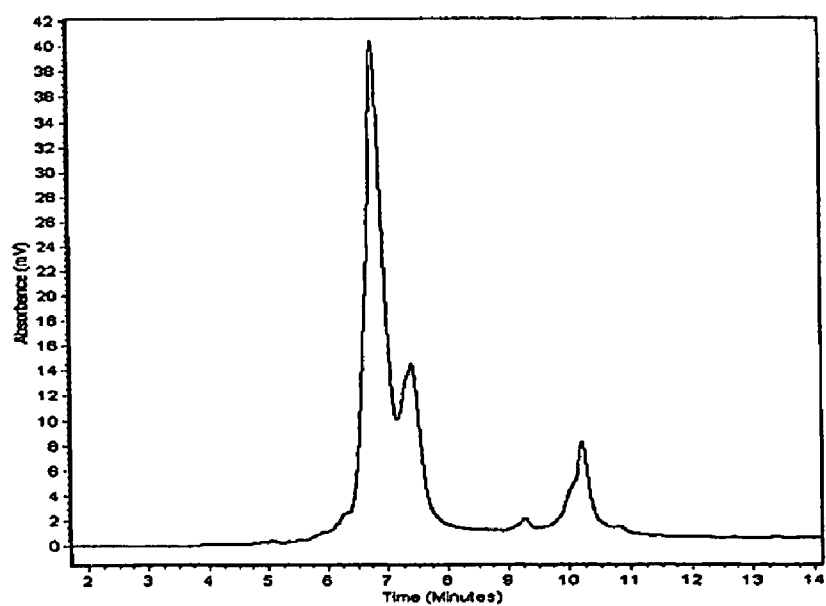
Figure 6C:
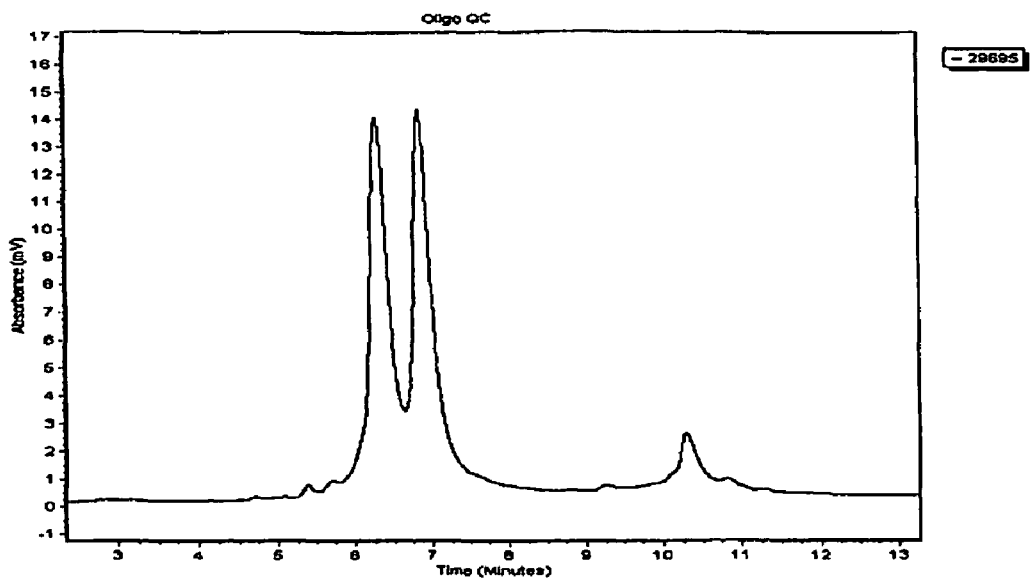
Figure 6D:
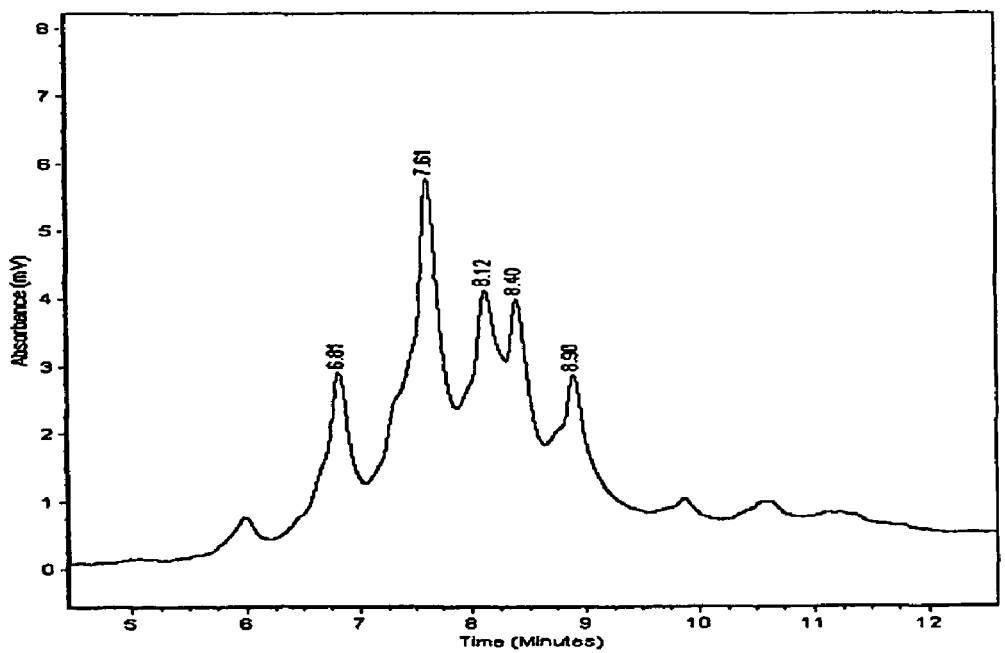

Nucleic Acid Fragment Analysis System (Transgenomic, USA). The column temperature was set at 80° C. and the probes were washed in gradient acetonitrile buffer. The eluant was detected at 260 nM using an ultra violet detector. The number and shape of the peaks eluted over time indicated the quality of the probes. As shown in FIG. 5, the useful content of 5A and 5B is 93.35% and 64.8% respectively.

Example 3

The probes in table 1 were used as HLA_A, B, DRB1 genotyping probes. PBH_0301xxx represent the HLA-A probes, PBH_0302xxx represent HLA-B probes and PBH_0303xxx represent the HLA-DRB1 probes.

Example 4

Cloning of HLA standard alleles, the procedure are as following:

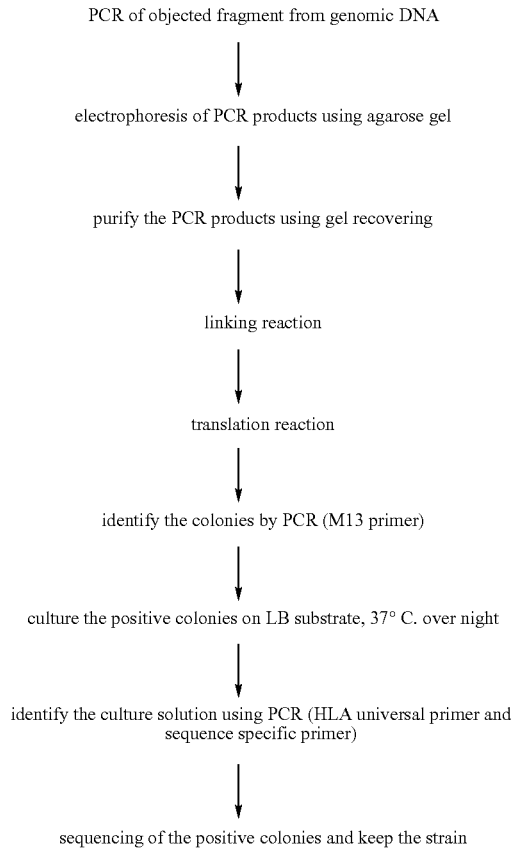

A HLA standard gene bank was constructed for detecting the HLA_A, B, DRB1 genotyping probes and QC of HLA chips. There are 43 HLA-A alleles have been cloned which distributed to 19 allele groups and covering 95.0% of the medium types; For HLA_B, 47 alleles have been cloned which distributed to 29 allele groups and covering 80% of the medium types; For HLA_DR, 22 alleles have been cloned which contributed to 14 allele groups and covering 87.5% of the medium types. The probes in table 1 were designed based on the allele sequences of 12th IHWG (www.ihwg.org). Then the probes were immobilized on chemical modified slides to fabricate HLA chips.

The hybridization and washing conditions should be keep a strong positive signal and a relatively weak false positive signal. The temperature of hybridization and washing were 65° C. and 45° C. respectively, and the ion strength was 0.2% SDS, 0.1×SSC.

The samples containing target gene were hybridized with HLA chips, then through washing and scanning the data were gain and the genotype was detected. For example, 5 μl PCR product and 5 μl hybridization buffer were mixed then hybridized 1 hr at 65° C., and then washing the chip using a solution containing 0.2% SDS and 0.1×SSC10 min at 45° C., washing 5 min again using 1×SSC, rinsed in water for 1 min. Then the chip was dried with centrifuging, scanned with a scanner. The photo was treated and the data were analyzed using HLA specific software and the genotype result was produced.

The probes for HLA-A, B, DRB1 genotyping have been shown in table 1.

TABLE 1

The genotyping probes for HLA_A, B, DRB1 locus

| Probe name | sequences | SEQ ID NO: |
|---|---|---|
| HLA_A probes | | |
| PBH_0301001 | CCTGCGCTCTTGGACCGC | 1 |
| PBH_0301001a | CCTGCGCTCTTGGACCGCG | 2 |
| PBH_0301001b | CCTCCTGCGCTCTTGGACCG | 3 |
| PBH_0301001c | CCTGGGCTCTTGGACC | 4 |
| PBH_0301001d | CGTGTCCCGGCCCGGC | 5 |
| PBH_0301001e | ATGGAGCCGGGGCGC | 6 |
| PBH_0301001g | CCTGCGCTCTTGGAGCGCGG | 7 |
| PBH_0301001comp | GCGGTCCAAGAGCGCAGG | 8 |
| PBH_0301002a | CCTGCGCTTTTGGACCGC | 9 |
| PBH_0301002B | GGTGCGCTGTTGGACCGC | 10 |
| PBH_0301003 | GCAGGAGAGGCCTGAGTATTGG | 11 |
| PBH_0301004 | CACCATCAGATAATGTATGGCTGC | 12 |
| PBH_0301004 | CACCATCCAGATAATGTATGGCTGC | 13 |
| PBH_0301101 | TTCTACACCTCCGTGTCCCG | 14 |
| PBH_0301103 | CGCTTCATCGCAGTGGGCT | 15 |
| PBH_0301105 | CGAGCCAGAAGATGGAGCC | 16 |
| PBH_0301106 | CCGCGGGCACCGTGGATA | 17 |
| PBH_0301107 | GCAGGAGGGTCCGGAGTATT | 18 |
| PBH_0301111 | GACGTGGGGCCGGACGGG | 19 |
| PBH_0301112 | GACGGGCGCCTCCTCCGC | 20 |
| PBH_0301114 | CGGGTACCACCAGTACGCCT | 21 |
| PBH_0301115 | GGTACCGGCAGGACGCCTA | 22 |
| PBH_0301116 | CGCCCTGAACGAGGACCTG | 23 |
| PBH_0301117 | CGGACATGGCAGCTCAGATC | 24 |
| PBH_0301119 | CCACCAAGCACAAGTGGGA | 25 |
| PBH_0301120 | AAGTGGGAGACGGCCCATG | 26 |
| PBH_0301121 | AGGCGGCCCGTGTGGCGG | 27 |
| PBH_0301122 | AGGCGGTCCATGCGGCGG | 28 |
| PBH_0301123 | CGGCCCATGAGGCGGAGC | 29 |
| PBH_0301125 | TACCTGGATGGCACGTGCG | 30 |
| PBH_0301127 | CTGGAGGGCGAGTGCGTGG | 31 |
| PBH_0301128 | TGCGTGGACGGGCTCCGC | 32 |
| PBH_0301129 | GTATTTCTACACCTCCGTGTCCCG | 33 |
| PBH_0301130 | CGAGCGGTTTGACAGCGAC | 34 |
| PBH_0301131 | CGTGCGGTTCGACAGCGAC | 35 |
| PBH_0301133 | CGTGGGGCCGGACGGG | 36 |
| PBH_0301136 | AGGCGGTCCATGCGGCG | 37 |
| PBH_0301137 | CCCGGCCGCGGGGAGCCC | 38 |
| PBH_0301138 | CCGCGGGCGCCGTGGATA | 39 |
| PBH_0301139 | TGGGACGAGGAGACAGGGA | 40 |
| PBH_0301140 | TGGGACCAGGAGACACGGA | 41 |
| PBH_0301141 | TGGGGACCCTGCGCGGCTA | 42 |
| PBH_0301142 | GACGTGGGGTCGGACGGG | 43 |
| PBH_0301143 | GACGGGCGCTTCCTCCGC | 44 |
| PBH_0301144 | GCGGGTACCAGCAGGACGC | 45 |
| PBH_0301145 | CGCCCTGAAAGAGGACCTG | 46 |
| PBH_0301146 | AGCTCAGATCACCAAGCGCA | 47 |
| PBH_0301146a | TCAGATCACGAAGCGCAAGAG | 48 |
| PBH_0301147 | AGCTCAGATGACCGAGCGCA | 49 |
| PBH_0301148 | GGCTCAGATCACCCAGCGCA | 50 |

TABLE 1-continued

The genotyping probes for HLA_A, B, DRB1 locus

| Probe name | sequences | SEQ ID NO: |
|---|---|---|
| PBH_0301148a | TCAGATCACCCAGCGCAAGTG | 51 |
| PBH_0301149 | AGACGGCCCATGAGGCG | 52 |
| PBH_0301149a | AGACGGCCCATGAGGCGG | 53 |
| PBH_0301150 | GCGGAGCAGCGGAGAGTCT | 54 |
| PBH_0301150a | AGACGCCCATGAGGCGG | 55 |
| PBH_0301151 | GCGGAGCAGTTGAGAGCCT | 56 |
| PBH_0301151a | GGCGGAGCAGTTGAGAGCC | 57 |
| PBH_0301152 | GCGGAGCAGTGGAGAGCcT | 58 |
| PBH_0301153 | TACCTGGAGGGCACGTGCG | 59 |
| PBH_0301154 | TGCGTGGAGTGGCTCCGC | 60 |
| PBH_0301155 | TCACCGAGTGGACCTGGGG | 61 |
| PBH_0301155a | CCGAGTGGACCTGGGGACC | 62 |
| PBH_0301156 | TGACCGAGAGAACCTGCGG | 63 |
| PBH_0301156a | CCGAGAGAACCTGCGGATCG | 64 |
| PBH_0301157 | GAAGGCCCACTCACAGACTG | 65 |
| PBH_0301171 | TATTTCTTCACATCCGTGTCCCG | 66 |
| PBH_0301172 | TCTACACTTCCGTTTCCCGGC | 67 |
| PBH_0301173 | CTACACCTCCATGTCCCGGC | 68 |
| PBH_0301174 | CCGGAACACACGGAAAGTGAA | 69 |
| PBH_0301175 | ATTGGGACGGGAGACACG | 70 |
| PBH_0301176 | GACACGGAATATGAAGGCCCA | 71 |
| PBH_0301177 | GACACGGAATGTGAAGGCCC | 72 |
| PBH_0301178 | TCACAGACTCACCGAGTGGACC | 73 |
| PBH_0301179 | TCACAGATTGACCGAGTGGACC | 74 |
| PBH_0301180 | TCACAGACTGACCGAGTGGACC | 75 |
| PBH_0301181 | CGAGCGAACCTGGGGACC | 76 |
| PBH_0301182 | CCGAGAGAGCCTGCGGATC | 77 |
| PBH_0301183 | ACCGAGAGAACCTGGGGACC | 78 |
| PBH_0301184 | GTGGACCTGGCGACCCTGC | 79 |
| PBH_0301185 | CACCGTCCAGAGGATGTATGGC | 80 |
| PBH_0301186 | ACCAGCAGGACGCTTACGACG | 81 |
| PBH_0301187 | TCGCCTTGAACGAGGACCTG | 82 |
| PBH_0301188 | CCTGCGCTCTTGGACCGC | 83 |
| PBH_0301189 | TCAGACCACCAAGCACAAGTGG | 84 |
| PBH_0301190 | GAGGCGGCCCATGTGGC | 85 |
| PBH_0301191 | GGCCATGCGGCGGAGC | 86 |
| PBH_0301192 | GCGGCCCGTCGGCGGA | 87 |
| PBH_0301193 | GCACGTGCGTGGAGTGGC | 88 |
| PBH_0301194 | GCCGGTGCGTGGACGGGC | 89 |
| PBH_0301195 | GGCGAGTGCGTGGAGTGGC | 90 |
| PBH_0301196 | GCACGTGCGTGGACGGGC | 91 |
| PBH_0301197 | GCCGGTGCGTGGAGTGGC | 92 |
| PBH_0301198 | GGCGAGTGCGTGGACGGGC | 93 |
| PBH_0301199 | AGACACGGAAAGTGAAGGCCC | 94 |

HLA_Bprobe

| Probe name | sequences | SEQ ID NO: |
|---|---|---|
| PBH_0302001 (positive) | TGGCCCTGACCGAGACCTGGGC | 95 |
| PBH_0302001a | CTACAACCAGAGCGAGGCCG | 96 |
| PBH_0302002 (negative) | GCCCTGACCCAGACCTGGG | 97 |
| PBH_0302003 | CCCGAACCTCCTCCTGC | 98 |
| PBH_0302004 | CCCGAACCGTCCTCCTGC | 99 |
| PBH_0302005 | TGCTCTCGGCGGCCCTG | 100 |
| PBH_0302006 | TGCTCTCGGGAGCCCTGG | 101 |
| PBH_0302007 | GGGGGCAGTGGCCCT | 102 |
| PBH_0302008 | TGAGGTATTTCGACACCGCCA | 103 |
| PBH_0302009 | TGAGGTATTTCTACACCGCCATG | 104 |
| PBH_0302010 | TTTTCCACACCTCCGTGTCcC | 105 |
| PBH_0302011 | TCTACACCGCCATGTCCCG | 106 |
| PBH_0302012 | TCTACACCTCCGTGTCCCGG | 107 |
| PBH_0302013 | CCGCTTCATCTCAGTGGGCTAC | 108 |
| PBH_0302014 | CGCTTCATCACCGTGGGCT | 109 |
| PBH_0302015 | CGCTTCATCGCAGTGGGCT | 110 |
| PBH_0302016 | TACGTGGACGGCACCCAGTT | 111 |
| PBH_0302017 | CGTGGACGACACCCAGTTCG | 112 |
| PBH_0302018 | GGACGACACGCTGTTCGTGA | 113 |
| PBH_0302019 | TGGACGACACGCAGTTCGTG | 114 |
| PBH_0302020 | GCGACGCCACGAGTCCG | 115 |
| PBH_0302021 | GCGACGCCGCGAGTCC | 116 |
| PBH_0302022 | GAGTCCGAGAGAGGAGCCGC | 117 |
| PBH_0302023 | CCGAGGAAGGAGCCGCG | 118 |
| PBH_0302024 | AGGATGGCGCCCCGG | 119 |
| PBH_0302025 | GGACGGAGCCCCGGGC | 120 |
| PBH_0302026 | CGGGCGCCGTGGATAGAG | 121 |
| PBH_0302027 | CGGGCGCCATGGATAGAG | 122 |
| PBH_0302028 | GGGGCGGGAATATTGGGAC | 123 |
| PBH_0302029 | GGGGCGGGAGTATTGGGAC | 124 |
| PBH_0302030 | GGGACCGGGAGACACAGATCT | 125 |
| PBH_0302031 | TGGGACCGGAACACACAGATC | 126 |
| PBH_0302032 | ACACAGAAGTAGAAGGGCCAGG | 127 |
| PBH_0302033 | ACACGGAACATGAAGGCCTCC | 128 |
| PBH_0302034 | CACACAGATCTTCAAGACCAACAC | 129 |
| PBH_0302035 | ATCTGCAAGGCCAAGGCACA | 130 |
| PBH_0302036 | TACAAGGCCCAGGCACAGACT | 131 |
| PBH_0302037 | ACACAGACTGACCGAGAG | 132 |
| PBH_0302038 | CACACAGACTTACCGAGAGAGCC | 133 |
| PBH_0302039 | GCACCGCGCTCCGCTA | 134 |
| PBH_0302040 | CGGACCCTGCTCCGCTACT | 135 |
| PBH_0302041 | ACCTGCGGATCGCGCTC | 136 |
| PBH_0302042 | CGGAACCTGCGCGGCT | 137 |
| PBH_0302043 | CGGGTCTCACATCATCCAGAGG | 138 |
| PBH_0302044 | GGGTCTGACACCCTCCAGAGG | 139 |
| PBH_0302045 | TCACACTTGGCAGACGATGTATG | 140 |
| PBH_0302046 | ACACCCTCCAGAGGATGTACGG | 141 |
| PBH_0302047 | CGACCTGGGGCCCGAC | 142 |
| PBH_0302048 | CGACGTGGGGCCGGAC | 143 |
| PBH_0302049 | GGGTACCACGAGGACGCCT | 144 |
| PBH_0302050 | CGGGTATGACCAGGACGCC | 145 |
| PBH_0302051 | GGGCATGACCAGTCCGGC | 146 |
| PBH_0302052 | GCGGGTATAACCAGTTCGCC | 147 |
| PBH_0302053 | GAGGACCTGCGCTCCTGGA | 148 |
| PBH_0302054 | GAGGACCTGAGCTCCTGGA | 149 |
| PBH_0302055 | GGACCGCCGCGGACAC | 150 |
| PBH_0302056 | GGACCGCGGCGGACAC | 151 |
| PBH_0302057 | CGGACACGGGGCTCAG | 152 |
| PBH_0302058 | CGGACACCGCGGCTCAG | 153 |
| PBH_0302059 | GGCCCGTGAGGCGGAG | 154 |
| PBH_0302060 | GGCCCGTGTGGCGGAG | 155 |
| PBH_0302061 | GCGGAGCAGGACAGAGCCTA | 156 |
| PBH_0302062 | GCGGAGCAGTGGAGAGCCTA | 157 |
| PBH_0302063 | GCGGAGCAGCTGAGAGCCTA | 158 |
| PBH_0302064 | AGCAGCTGAGAACCTACCTGGAG | 159 |
| PBH_0302065 | AGCAGCTGAGAGCCTACCTGGAG | 160 |
| PBH_0302066 | GGAGGGCGAGTGCGTGG | 161 |
| PBH_0302067 | GGAGGGCACGTGCGTGG | 162 |
| PBH_0302068 | GGAGGGCCTGTGCGTGG | 163 |
| PBH_0302069 | CGTGGAGTCGCTCCGCAG | 164 |
| PBH_0302070 | CGTGGAGTGGCTGCGCAG | 165 |
| PBH_0302071 | CTCCGCAGACACCTGGAGAAC | 166 |
| PBH_0302072 | GCTCGCGCAGATACCTGGAGAA | 167 |
| PBH_0302073 | AGGACAAGCTGGAGCGCG | 168 |
| PBH_0302074 | GGACACGCTGGAGCGCG | 169 |
| PBH_0302075 | GGAGACGCTGCAGCGCG | 170 |

HLA_DRB1probe

| Probe name | sequences | SEQ ID NO: |
|---|---|---|
| PBH_0303001 | CTTGTGGCAGCTTAAGTTTGAATGT | 171 |
| PBH_0303002 | TGGAGTACTCTACGTCTGAGTGTCA | 172 |
| PBH_0303003 | GGAGCAGGTTAAACATGAGTGT | 173 |
| PBH_0303004 | CCTGTGCAGGGTAAGTATAAGT | 174 |
| PBH_0303005 | TTGGAGTACTCTACGGGTGAGTG | 175 |
| PBH_0303006 | CCTGTGGCAGCCTAAGAGGG | 176 |
| PBH_0303007 | CCTGGAGCAGGCGCGG | 177 |
| PBH_0303008 | CCTGGAAGACGAGCGGGC | 178 |
| PBH_0303009 | CCAGGAGGAGAACGTGCGC | 179 |
| PBH_0303010 | CCTGGAAGACAGGCGGGC | 180 |
| PBH_0303011 | CGGTTGTGGAAAGATGCATC | 181 |
| PBH_0303012 | CGGTTCCTGGACAGATACTTCTATCAC | 182 |
| PBH_0303013 | TGCAGTTCCTGGAAAGACTTTCT | 183 |
| PBH_0303014 | CGGTATGTGCACAGAGGCATCT | 184 |
| PBH_0303015 | TGCTGAAAGACGAGTCA | 185 |
| PBH_0303016 | CGGTTACTGGAGAGACACTTCCATA | 186 |
| PBH_0303017 | CGGCCTGATGAGGAGTACTGG | 187 |
| PBH_0303018 | CCTGTCGCCGAGTCCTGGA | 188 |
| PBH_0303019 | GGCCTGATGCCGAGTACTGG | 189 |
| PBH_0303020 | CAGGAGGAGCTCCTGCGCTT | 190 |

TABLE 1-continued

The genotyping probes for HLA_A, B, DRB1 locus

| Probe name | sequences | SEQ ID NO: |
|---|---|---|
| PBH_0303021 | GAGCAGAAGCGGGGCCGG | 191 |
| PBH_0303022 | TCCTGGAGCGGAGGCGG | 192 |
| PBH_0303023 | GCGGGCCCTGGTGGACA | 193 |
| PBH_0303024 | GGGGGAGTTCCGGGCGG | 194 |
| PBH_0303025 | GGGGGAGTACCGGGCGG | 195 |
| PBH_0303026 | GGCCTGACGCTGAGTACTGG | 196 |
| PBH_0303027 | CAATGGGACGGAGCGGGTGC | 197 |
| PBH_0303027a | AATGGGACGGAGCGGGTG | 198 |
| PBH_0303027b | GGGACGGAGCGGGT | 199 |
| PBH_0303028 | GGGGGAGTTCCGGGCG | 200 |
| PBH_0303029 | TGGGGGAGTACCGGGCG | 201 |
| PBH_0303030 | ACCAAGAGGAGTACGTGCGCTT | 202 |
| PBH_0303031 | GCCTGCTGCGGAGCACTG | 203 |
| PBH_0303032 | CCAGGAGGAGTTCGTGCGG | 204 |
| PBH_0303033 | GCTGGAAGACGAGCGGGC | 205 |
| PBH_0303034 | GCCTGCTGCGGAGCACTG | 206 |
| PBH_0303035 | GGCCTGATGCCGAGTACTGG | 207 |
| PBH_0303036 | CCAGGAGGAGAACGTGCGC | 208 |

TABLE 1-continued

The genotyping probes for HLA_A, B, DRB1 locus

| Probe name | sequences | SEQ ID NO: |
|---|---|---|
| PBH_0303037 | CCTGGAAGACGAGCGGGC | 209 |
| PBH_0303038 | GACAGGCGCGCCGCG | 210 |
| PBH_0303039 | CTGGAGCAGAGGCGGGC | 211 |
| PBH_0303040 | AACCAAGAGGAGTACGTGCGC | 212 |
| PBH_0303041 | AATGGGACGCAGCGGBT | 213 |
| PBH_0303055 | CATCCTGGAAGACGAGCGGGG | 214 |

Example 5

An array of HLA typing, there are 64 detection probes, 2 positive probes, 1 negative probes, 1 hybridization control negative probes, 1 hybridization control positive probes. As shown in table 2, the italic letters represent the control probes and the others are detection probes. Table 3 has shown an example of the arrangement of the probes in HLA chip.

TABLE 2

The arrangement of the probes in a microarray

| Hybridization Control (positive) | Hybridization Control (positive) | Detection probe 1 | Detection probe 1 | Detection probe 2 | Detection probe 2 | Detection probe 3 | Detection probe 3 | Detection probe 4 | Detection probe 4 | Hybridization Control (positive) | Hybridization Control (positive) |
|---|---|---|---|---|---|---|---|---|---|---|---|
| Hybridization Control (negative) | Hybridization Control (negative) | Detection probe 5 | Detection probe 5 | Detection probe 6 | Detection probe 6 | Detection probe 7 | Detection probe 7 | Detection probe 8 | Detection probe 8 | Hybridization Control (negative) | Hybridization Control (negative) |
| Positive (1) | Positive (1) | Detection probe 9 | Detection probe 9 | Detection probe 10 | Detection probe 10 | Detection probe 11 | Detection probe 11 | Detection probe 12 | Detection probe 12 | positive (1) | positive (1) |
| Positive (2) | Positive (2) | Detection probe 13 | Detection probe 13 | Detection probe 14 | Detection probe 14 | Detection probe 15 | Detection probe 15 | Detection probe 16 | Detection probe 16 | positive (2) | positive (2) |
| negative | negative | Detection probe 17 | Detection probe 17 | Detection probe 18 | Detection probe 18 | Detection probe 19 | Detection probe 19 | Detection probe 20 | Detection probe 20 | negative | negative |
| Detection probe 53 | Detection probe 53 | Detection probe 21 | Detection probe 21 | Detection probe 22 | Detection probe 22 | Detection probe 23 | Detection probe 23 | Detection probe 24 | Detection probe 24 | Detection probe 57 | Detection probe 57 |
| Detection probe 54 | Detection probe 54 | Detection probe 25 | Detection probe 25 | Detection probe 26 | Detection probe 26 | Detection probe 27 | Detection probe 27 | Detection probe 28 | Detection probe 28 | Detection probe 58 | Detection probe 58 |
| Detection probe 55 | Detection probe 55 | Detection probe 29 | Detection probe 29 | Detection probe 30 | Detection probe 30 | Detection probe 31 | Detection probe 31 | Detection probe 32 | Detection probe 32 | Detection probe 59 | Detection probe 59 |
| Detection probe 56 | Detection probe 56 | Detection probe 33 | Detection probe 33 | Detection probe 34 | Detection probe 34 | Detection probe 35 | Detection probe 35 | Detection probe 36 | Detection probe 36 | Detection probe 60 | Detection probe 60 |
| negative | negative | Detection probe 37 | Detection probe 37 | Detection probe 38 | Detection probe 38 | Detection probe 39 | Detection probe 39 | Detection probe 40 | Detection probe 40 | negative | negative |
| Positive (2) | Positive (2) | Detection probe 41 | Detection probe 41 | Detection probe 42 | Detection probe 42 | Detection probe 43 | Detection probe 43 | Detection probe 44 | Detection probe 44 | Positive (2) | Positive (2) |
| Positive (1) | Positive (1) | Detection probe 45 | Detection probe 45 | Detection probe 46 | Detection probe 46 | Detection probe 47 | Detection probe 47 | Detection probe 48 | Detection probe 48 | Positive (1) | Positive (1) |
| Hybridization Control (negative) | Hybridization Control (negative) | Detection probe 49 | Detection probe 49 | Detection probe 50 | Detection probe 50 | Detection probe 51 | Detection probe 51 | Detection probe 52 | Detection probe 52 | Hybridization Control (negative) | Hybridization Control (negative) |
| Hybridization Control (positive) | Hybridization Control (positive) | Detection probe 61 | Detection probe 61 | Detection probe 62 | Detection probe 62 | Detection probe 63 | Detection probe 63 | Detection probe 64 | Detection probe 64 | Hybridization Control (positive) | Hybridization Control (positive) |

TABLE 3

The arrangement of the probes in a HLA typing array

| | | | | | | | | | | | |
|---|---|---|---|---|---|---|---|---|---|---|---|
| Hex A001comp A030 | A001comp | A001comp | Control blank A009 | blank | blank | A062-1 175 A062-2 | 175 | 175 | IC1 A03Control1 IC2 A03Control3 | A03Control1 A03Control3 | A03Control1 A03Control3 |
| 159a | 159a | 159a | 171a | 171a | 171a | 139a | 139 | 139 | A001a | A001a | A001a |
| 159b | 159b | 159b | 129 | 129 | 129 | 139b | 139b | 139b | A001 | A001 | A001 |
| A001 A076 | A001 | A001 | 172 | 172 | 172 | 139a | 139a | 139a | Negative | Negative | Negative |
| 156 | 156 | 156 | A114 115 | 115 | 115 | 140 A065 | 140 | 140 | A002b | A002b | A002b |
| 181 | 181 | 181 | 144 | 144 | 144 | 174a | 174a | 174a | A070 | | |
| 182 A074 | 182 | 182 | 114 | 114 | 114 | 174b | 174b | 174b | 157 | 157 | 157 |
| 178 | 178 | 178 | A080 141a | 141a | 141a | A148 190 | 190 | 190 | 162 A156 | 162 | 162 |
| 180a Negative | 180a | 180a | 141 A111 | 141 | 141 | 192 121a | 192 121a | 192 121a | 151b 152a | 151b 152a | 151b 152a |
| A002b | A002b | A002b | 143a | 143a | 143a | A161 125 | 125 | 125 | 152b*k29698 | 152b*k29698 | 152b*k29698 |
| A001 | A001 | A001 | 112 | 112 | 112 | 153 | 153 | 153 | A001 | A001 | A001 |
| A001a IC2 | A001a | A001a** | A142 148b | 148b | 148b | A163 | | | A166 | | |
| A03Control3 IC1 | A03Control3 | A03Control3 | 146b Control | 146b blank | 146b blank | 195b 195a | 195b 195a | 195b 195a | 128 154 Hex A001comp | 128 154 Hex A001comp | 128 154 A001comp |
| A03Control1 | A03Control1 | A03Control1 | blank | | | | | | | | |

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

---

The invention claimed is:

1. A method for medium resolution typing of a target human leukocyte antigen (HLA) gene comprising:
   a) isolating a target leukocyte cell comprising a target HLA gene from a suitable sample and obtaining a preparation comprising a target HLA nucleotide sequence that is at least a part of said target HLA gene from said isolated target leukocyte cell and, optionally another nucleotide sequence not related to said target HLA gene;
   b) providing a chip comprising a support suitable for use in nucleic acid hybridization having immobilized thereon: a set of oligonucleotide probes complementary to said target HLA nucleotide sequence, each of said probes having 30 nucleotides or less, wherein said set of oligonucleotide probes comprises SEQ ID NOS: 1-214 or the complement of SEQ ID NOS: 1-214; and at least one of each of the following oligonucleotide control probes: a positive control probe, a negative control probe, a hybridization control probe and an immobilization control probe; and
   c) hybridizing said preparation obtained in step a) to said chip provided in step b) and assessing hybridization between said target HLA nucleotide sequence and/or said another nucleotide sequence and said probe comprised on said chip to determine the type of said target HLA gene.

2. The method of claim 1, wherein the suitable sample is selected from the group consisting of blood, saliva, hair, a human tissue that comprises a human nucleic acid, and any other human tissues containing nuclear cells.

3. The method of claim 1, wherein the target leukocyte cell is isolated from the suitable sample using a magnetic microbead.

4. The method of claim 1, wherein the preparation of the target HLA nucleotide sequence comprises a nucleic acid amplification step.

5. The method of claim 1, wherein the target HLA nucleotide sequence obtained in step a) is single-stranded DNA or RNA.

6. The method of claim 1, wherein a labeled target HLA nucleotide sequence is obtained in step a).

7. The method of claim 1, wherein the another nucleotide sequence is complementary to the positive control probe, the negative control probe or the hybridization control probe comprised on the chip.

8. The method of claim 1, wherein the probes comprised on the chip are modified.

9. The method of claim 1, wherein the chip comprises 400 different types of probes.

10. The method of claim 1, wherein the chip comprises multiple arrays of probes and each array comprises 400 different types of probes.

11. The method of claim 1, wherein multiple copies of a probe are immobilized on the chip.

12. The method of claim 1, wherein the positive control probe is: complementary to a portion of the target HLA nucleotide sequence; a nucleotide sequence amplified synchronically with the target HLA nucleotide sequence or; a synthetic nucleotide sequence.

13. The method of claim 12, wherein the negative control probe has about 1-3 basepair mismatches when compared to the positive control probe.

14. The method of claim 1, wherein the hybridization control probe is complementary to a synthetic nucleotide sequence not related to the target HLA gene.

15. The method of claim 1, wherein one end of the immobilization control probe is chemically modified and the other end of the immobilization control probe has a detectable label.

16. The method of claim 1, wherein the hybridization reaction in step c) is conducted in a hybridization solution comprising sodium chloride/sodium citrate (SSC) and a surfactant.

17. The method of claim 1, wherein the hybridization reaction in step c) is conducted at a temperature ranging from about 42° C. to about 70° C.

18. The method of claim 1, wherein the immobilization efficiency is assessed by analyzing a signal from the immobilization control probe.

19. The method of claim 1, wherein the overall hybridization efficiency is assessed by analyzing the hybridization between the hybridization control probe and a labeled synthetic nucleotide sequence not related to the target HLA gene.

20. The method of claim 1, wherein the hybridization specificity is assessed by analyzing the ratio between the hybridization signal involving the positive control probe and the hybridization signal involving the negative control probe, and the ratio between the hybridization signal involving the positive hybridization control probe and the hybridization signal involving the negative hybridization control probe, and increased ratios indicating the increased hybridization specificity.

21. The method of claim 1, wherein, in hybridizations involving a group of closely related probes, a positive signal(s) is determined based on the following criteria:
   a) the ratio of the hybridization signal over background noise is more than 3;
   b) the ratio of the hybridization signal over a relevant positive control probe hybridization signal is within a predetermined range;
   c) comparing hybridization signals of all probes giving positive signals based on the steps of a) and b), or hybridization signals of two probes giving two strongest hybridization signals when only one probe giving positive signal based on the steps of a) and b), to determine whether the signal is positive or negative; and d) there are 2 or less than 2 positive signals involving the group of closely related probes.

22. The method of claim 1, wherein the chip comprises an HLA-A probe, an HLA-B probe, and an HLA-DRB1 probe.

23. The method of claim 1, wherein multiple positive control probes are immobilized on the chip, and variations in length and sequence of the immobilized positive control probes, when hybridized with the target HLA nucleotide sequence or the another nucleotide sequence in the preparation provided in step a), create a group of hybridization signals having strong-to-weak or weak-to-strong orderly magnitude.

* * * * *